(12) United States Patent
Hara et al.

(10) Patent No.: US 6,348,478 B1
(45) Date of Patent: Feb. 19, 2002

(54) BIPHENYLAMIDINE DERIVATIVES

(75) Inventors: Takayuki Hara; Tomohisa Nakada; Yasunobu Takano; Satoshi Sugiura; Takaharu Tsutsumi; Yoshiharu Takazawa; Reiko Takarada, all of Hino (JP)

(73) Assignee: Teijin Limited, Osaka (JP)

( * ) Notice: Subject to any disclaimer, the term of this patent is extended or adjusted under 35 U.S.C. 154(b) by 0 days.

(21) Appl. No.: 09/554,449

(22) PCT Filed: Nov. 19, 1998

(86) PCT No.: PCT/JP98/05210

§ 371 Date: May 15, 2000

§ 102(e) Date: May 15, 2000

(87) PCT Pub. No.: WO99/26919

PCT Pub. Date: Jun. 3, 1999

(30) Foreign Application Priority Data

Nov. 20, 1997 (JP) ............................................... 9-319696

(51) Int. Cl.$^7$ ........................ C07D 213/55; A61K 31/44
(52) U.S. Cl. ........................ 514/349; 514/415; 514/637; 546/300; 548/469; 564/244
(58) Field of Search ........................ 546/300; 548/469; 564/244; 514/349, 415, 637

(56) References Cited

FOREIGN PATENT DOCUMENTS

| JP | 4-264068 | 9/1992 |
| JP | 4-334351 | 11/1992 |
| JP | 6-50977 | 2/1994 |
| JP | 10-1647 | 1/1998 |

OTHER PUBLICATIONS

17$^{th}$ Symposium on Medicinal Chemistry, 6$^{th}$ Annual Mtg. Of Division of Medicinal Chemistry 1997 Second Conference on Drug discovery, Abstracts 184–185, 1997.

International Search Report, Feb. 16, 1999.

*Primary Examiner*—Zinna Northington Davis
(74) *Attorney, Agent, or Firm*—Sughrue Mion, PLLC

(57) ABSTRACT

The present invention is a biphenylamidine derivative represented by the formula (1) or a pharmaceutically acceptable derivative thereof:

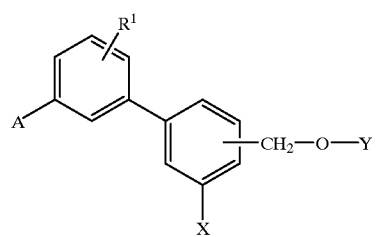

(1)

and the biphenylamidine derivative or the pharmaceutically acceptable derivative thereof is a novel compound which can be used as a clinically applicable FXa inhibitor.

10 Claims, No Drawings

BIPHENYLAMIDINE DERIVATIVES

RELATED APPLICATIONS

This application is a 35 U.S.C. § 371 filing of PCT/JP98/05210 filed on Nov. 19, 1998.

TECHNICAL FIELD

The present invention relates to a novel selective activated blood coagulation factor X (hereinafter referred to as [FXa]) inhibitor represented by the general formula (1).

BACKGROUND ART

The anticoagulant therapy plays an important role for thromboembolic diseases such as cardiac infarction, cerebral thrombosis, peripheral arterial thrombosis, and deep venous thrombosis as a medical treating preventing method.

Especially for preventing chronic thrombosis, a safe and suitable oral anticoagulant capable of being administered for a long period is needed. However, potassium warfarin, which is difficult to control its anticoagulation ability, is only available now, and a more easily usable anticoagulant has therefore been demanded.

Antithrombin agents have been developed as anticoagulants, but it has been known that the agents have a risk of causing hemorrhagic diathesis as a side effect, for example, on hirudine. It has been clarified that the inhibition of FXa placed in the upstream of thrombin is systematically more effective than the inhibition of the thrombin on a blood coagulation cascade, and it has further been clarified that FXa inhibitors are clinically preferable because of being weak in the side effect.

Biphenylamidine compounds expressing FXa-inhibiting activities are described in The 17th Symposium on Medicinal Chemistry, The 6th Annual Meeting of Division of Medicinal Chemistry, Abstracts, 184–185, 1997. The compounds of the present invention are novel compounds which are structurally clearly different from the biphenylamidine compounds at a point that a heteroatom is used to link a biphenylamidine structure which may interact with a S1 pocket, to a cyclic structure which may interact with an aryl-binding site.

And, cyclic imino derivatives (Japanese Unexamined Patent Publication (Kokai) Number 4-264068) disclose biphenylamidine derivatives, but the present invention is clearly different at a point that a heteroatom is bonded to the benzyl position.

Accordingly, the object of the present invention is to provide a novel compound which can be used as a clinically applicable FXa inhibitor.

DISCLOSURE OF THE INVENTION

The inventors of the present invention have extensively and intensively studied for achieving the above-mentioned object, and the following 1 to 10 have consequently been found out and led to the completion of the present invention.

1. A biphenylamidine derivative represented by the general formula (1), or a pharmaceutically acceptable salt thereof:

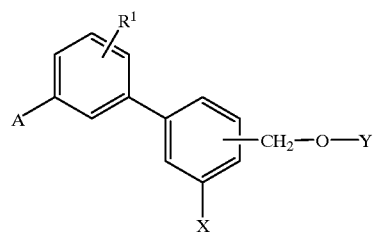

[wherein, A represents an amidino group; $R^1$ represents a hydrogen atom, a hydroxyl group, an amino group, a nitro group, a $C_1$–$C_8$ alkyl group, or a $C_1$–$C_8$ alkoxy group; X represents a carboxyl group, an aralkoxycarbonyl group, an aryloxycarbonyl group, a $C_1$–$C_8$ alkoxycarbonyl group, or a hydrogen atom (provided that Y is limited to a case represented by the below-mentioned formula (1-4) when X represents the hydrogen atom); Y represents a group of the following formula (1-1):

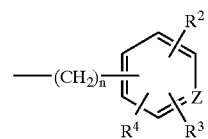

(wherein, n represents 0 or 1; Z represents C—H or a nitrogen atom; $R^2$ represents a hydrogen atom, an amino group, an amino $C_1$–$C_4$ alkyl group, a $C_1$–$C_4$ alkylamino group, or a di-$C_1$–$C_4$ alkylamino group; $R^3$ represents a hydrogen atom or a $C_1$–$C_4$ alkyl group; $R^4$ represents a hydrogen atom, a fluorine atom, a chlorine atom, a bromine atom, a hydroxide group, or a hydroxy $C_1$–$C_4$ alkyl group), or a group of the following formula (1-2):

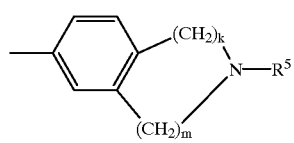

[wherein, k and m each represents an integer of from 0 to 2, provided that k+m≧2; $R^5$ represents a hydrogen atom, an amidino group, or a group of the following formula (1-3):

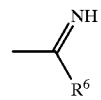

(wherein, $R^6$ represents a $C_1$–$C_4$ alkyl group, an aralkyl group, or a phenyl group)], or a group of the following formula (1-4):

(wherein, the wavy line represents an E isomer, a Z isomer, or their mixture on the basis of the double bond in an arbitrary ratio; $R^7$ represents a hydrogen atom or a trifluoroacetyl group)].

2. The above-mentioned biphenylamidine derivative represented by the general formula (2) or a pharmaceutically acceptable salt thereof:

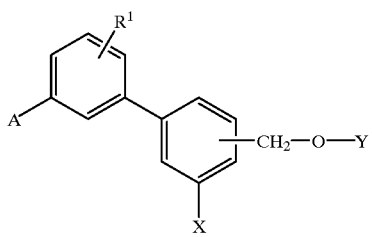

[wherein, A represents an amidino group; $R^1$ represents a hydrogen atom, a hydroxyl group, or a $C_1$–$C_4$ alkoxy group; X represents a carboxyl group, an aralkoxycarbonyl group, an aryloxycarbonyl group, a $C_1$–$C_8$ alkoxycarbonyl group, or a hydrogen atom, (provided that Y is limited to a case represented by the below-mentioned formula (2-4) when X represents the hydrogen atom); Y represents a group of the following formula (2-1):

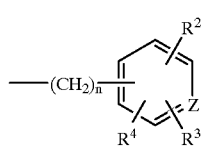

(wherein, n represents 0 or 1; Z represents C—H or a nitrogen atom; $R^2$ represents a hydrogen atom, an amino group, an amino $C_1$–$C_4$ alkyl group, a methylamino group, or a dimethylamino group; $R^3$ represents a hydrogen atom or a $C_1$–$C_4$ alkyl group; R4 represents a hydrogen atom, a chlorine atom, a hydroxyl group, a hydroxymethyl group, or a hydroxyethyl group), or a group of the following formula (2-2):

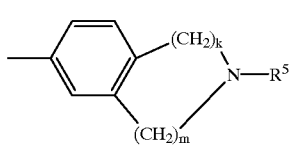

[wherein, k and m each represents an integer of from 0 to 2, (provided that k+m=2); $R^5$ is a hydrogen atom or a group of the following formula (2-3):

(wherein, $R^6$ represents a $C_1$–$C_4$ alkyl group)], or a group of the following formula (2-4):

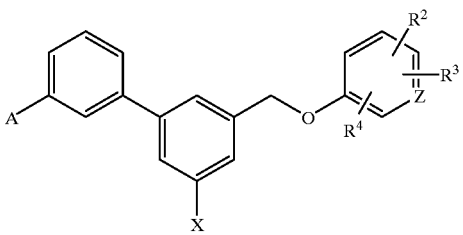

(wherein, the wavy line represents an E isomer, a Z isomer, or their mixture on the basis of the double bond in an arbitrary ratio; $R^7$ represents a hydrogen atom or a trifluoroacetyl group)].

3. The above-mentioned biphenylamidine derivative represented by the general formula (3) or a pharmaceutically acceptable salt thereof:

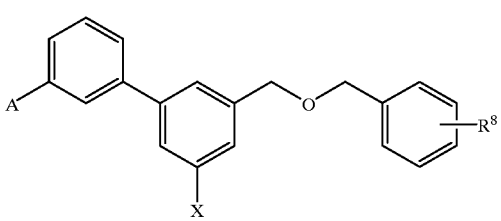

(wherein, A represents an amidino group; X represents a carboxyl group, an aralkoxycarbonyl group, an aryloxycarbonyl group, or a $C_1$–$C_8$ alkoxycarbonyl group; Z represents C—H or a nitrogen atom; $R^2$ represents a hydrogen atom, an amino group, an aminomethyl group, an aminoethyl group, a methylamino group, or a dimethylamino group; $R^3$ represents a hydrogen atom or a $C_1$–$C_4$ alkyl group; $R^4$ represents a hydrogen atom, a chlorine atom, a hydroxyl group, a hydroxymethyl group, or a hydroxyethyl group).

4. The above-mentioned biphenylamidine derivative represented by the general formula (4) or a pharmaceutically acceptable salt thereof:

(4)

(wherein, A represents an amidino group; X represents a carboxyl group, an aralkoxycarbonyl group, an aryloxycarbonyl group, or a $C_1$–$C_8$ alkoxycarbonyl group; $R^8$ represents a hydrogen atom, an amino group, an aminomethyl group, an aminoethyl group, or a $C_1$–$C_4$ alkyl group).

5. The above-mentioned biphenylamidine derivative represented by the general formula (5) or a pharmaceutically acceptable salt thereof:

(5)

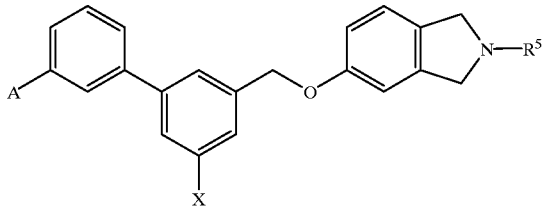

(wherein, A represents an amidino group; X represents a carboxyl group, an aralkoxycarbonyl group, an aryloxycarbonyl group, or a $C_1$–$C_8$ alkoxycarbonyl group; $R^5$ represents a hydrogen atom or an acetimidoyl group).

6. The above-mentioned biphenylamidine derivative represented by the general formula (6) or a pharmaceutically acceptable salt thereof.

(6)

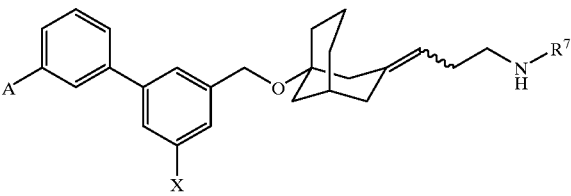

(wherein, the dashed line represents an E isomer, a Z isomer, or their mixture on the basis of the double bond in an arbitrary ratio; A represents an amidino group; X represents a carboxyl group, an aralkoxycarbonyl group, an aryloxycarbonyl group, a $C_1$–$C_8$ alkoxycarbonyl group, or a hydrogen atom; $R^7$ represents a hydrogen atom or a trifluoroacetyl group).

7. A prodrug compound which produces the mentioned biphenylamidine derivative or a pharmaceutically acceptable salt thereof, in vivo.

8. An anticoagulant inhibitor which comprises at least the above-mentioned biphenylamidine derivative or a pharmaceutically acceptable salt thereof and a pharmaceutically acceptable carrier.

9. A thrombus or embolus-preventing agent which comprises at least the above-mentioned biphenylamidine derivative or a pharmaceutically acceptable salt thereof and a pharmaceutically acceptable carrier.

10. A thrombus or embolus-treating agent which comprises at least the above-mentioned biphenylamidine derivative or a pharmaceutically acceptable salt thereof and a pharmaceutically acceptable carrier.

BEST MODE FOR CARRYING OUT THE INVENTION

The present invention is in detail disclosed below.

In the above-mentioned definition for the substituents of the compound of the general formula (1) according to the present invention.

The term "$C_1$–$C_4$ alkyl group" means a linear or branched carbon chain having one to four carbon atoms, such as methyl group, ethyl group, propyl group, isopropyl group, butyl group, isobutyl group, or tert-butyl group, preferably the group having one to three carbon atoms, particularly preferably methyl group or ethyl group.

The term "$C_1$–$C_8$ alkyl group" means a linear, branched or cyclic carbon chain having one to eight carbon atoms, such as methyl group, ethyl group, propyl group, isopropyl group, butyl group, isobutyl group, tert-butyl group, pentyl group, neopentyl group, isopentyl group, 1,2-dimethylpropyl group, hexyl group, isohexyl group, 1,1-dimethylbutyl group, 2,2-dimethylbutyl group, 1-ethylbutyl group, 2-ethylbutyl group, isoheptyl group, octyl group, isooctyl group, cyclopropyl group, cyclobutyl group, cyclopentyl group, cyclohexyl group, or the like, preferably the group having one to four carbon atoms, particularly preferably methyl group or ethyl group.

The term "$C_1$–$C_8$ alkoxy group" means, for example, methoxy group, ethoxy group, propoxy group, isopropoxy group, butoxy group, isobutoxy group, sec-butoxy group, tert-butoxy group, pentyloxy group, neopentyloxy group, tert-pentyloxy group, 2-methylbutoxy group, hexyloxy group, isohexyloxy group, heptyloxy group, isoheptyloxy group, octyloxy group, isooctyloxy group, or the like, preferably the group having one to four carbon atoms, most preferably methoxy group or ethoxy group.

The term "aralkoxycarbonyl group" bonded to the benzene ring as X means benzyloxycarbonyl group, 4-methoxybenzyloxycarbonyl group, 3-trifluoromethylbenzyloxycarbonyl group, 3-oxohydroisobenzofuranyloxycarbonyl group, or the like, preferably benzyloxycarbonyl group or 3-oxohydroisobenzofuranyloxycarbonyl group.

The term "aryloxycarbonyl group" means phenoxycarbonyl group, naphthyloxycarbonyl group, 4-methylphenoxycarbonyl group, 3-chlorophenoxycarbonyl group, 4-methoxyphenylcarbonyl group, indan-5-yloxycarbonyl group, or the like, preferably phenoxycarbonyl group or indan-5-yloxycarbonyl group.

The term "$C_1$–$C_8$ alkoxycarbonyl group" means methoxycarbonyl group, ethoxycarbonyl group, propoxycarbonyl group, isopropoxycarbonyl group, butoxycarbonyl group, isobutoxycarbonyl group, sec-butoxycarbonyl group, tert-butoxycarbonyl group, pentyloxycarbonyl group, isopentyloxycarbonyl group, neopentyloxycarbonyl group, hexyloxycarbonyl group, heptyloxycarbonyl group, octyloxycarbonyl group, or methoxycarbonyl group which is substituted by an acetoxy group, a pivaloyloxy group or a 5-methyl-3-oxo-2,4-dioxolenyl group, or the like, preferably methoxycarbonyl group, ethoxycarbonyl group, propoxycarbonyl group, isopropoxycarbonyl group, acetoxymethyloxycarbonyl group, pivaloyloxymethyloxycarbonyl group, (5-methyl-3-oxo-2,4-dioxonyl)methyloxycarbonyl group, or ethoxycarbonyloxyethoxycarbonyl group.

The term "amino $C_1$–$C_4$ alkyl group" means aminomethyl group, 1-aminoethyl group, 2-aminoethyl group, 1-aminopropyl group, 2-aminopropyl group, 3-aminopropyl group, 1-aminomethylethyl group, 1-aminobutyl group, 4-aminobutyl group, or the like, preferably aminomethyl group, 1-aminoethyl group or 2-aminoethyl group, more preferably aminomethyl group or 2-aminoethyl group.

The term "$C_1$–$C_4$ alkylamino group" means methylamino group, ethylamino group, propylamino group, isopropylamino group, butylamino group, isobutylamino group, sec-butylamino group, tert-butylamino group, or the like, preferably methylamino group, ethylamino group or propylamino group, more preferably methylamino group.

The term "di-$C_1$–$C_4$ alkylamino group" means dimethylamino group, methylethylamino group, methylisopropylamino group, diethylamino group, diisopropylamino group, dibutylamino group, or the like, preferably dimethylamino group.

The term "hydroxy $C_1$–$C_4$ alkyl group" means hydroxymethyl group, 1-hydroxyethyl group, 2-hydroxyethyl group, 1-hydroxypropyl group, 2-hydroxypropyl group, 3-hydroxypropyl group, 1-hydroxymethylethyl group, 1-hydroxybutyl group, 4-hydroxybutyl group, or the like, preferably hydroxymethyl group, 1-hydroxyethyl group or 2-hydroxyethyl group, more preferably hydroxymethyl group, or 2-hydroxyethyl group.

The compound (1) of the present invention forms acid addition salts in some cases, while the compound (1) forms salts with bases in dependence on the kinds of the substituents in other cases. Such the salts are particularly not limited, when the salts are pharmaceutically acceptable salts, and specifically include mineral acid salts such as hydrochloride, hydrobromide, hydroiodide, phosphate, nitrate, and sulfate; organic sulfonates such as methane sulfonate, 2-hydroxyethanesulfonate, and p-toluenesulfonate; and organic carboxylates such as acetate, trifluoroacetate, propionate, oxalate, malonate, succinate, glutarate, adipate, tartarate, maleate, malate, and mandelate as acid addition salts, and further include salts with inorganic bases, such as sodium salt, potassium salt, magnesium salt, calcium salt, and aluminum salt, and salts with organic bases, such as methylamine salt, ethylamine salt, lysine salt, and ornithine salt, as base addition salts.

The preferable compounds of the present invention are shown in the table 1.

The more preferable compounds are the compounds having the following compound numbers among the compounds shown in the table 1. 1, 8, 10, 18, 30, 32, 83, 88, 90, 92, 96, 97, 100, 108, 110, 111, 112, 113, 114, 122, 123, 173, 174.

A typical method for synthesizing the compound represented by the general formula (1) according to the present invention is explained below.

The present compound represented by the general formula (1), wherein $X^1$ represents a $C_1$–$C_4$ alkoxycarbonyl group or a hydrogen atom, can fundamentally be synthesized according to the following reaction formula.

scheme 1

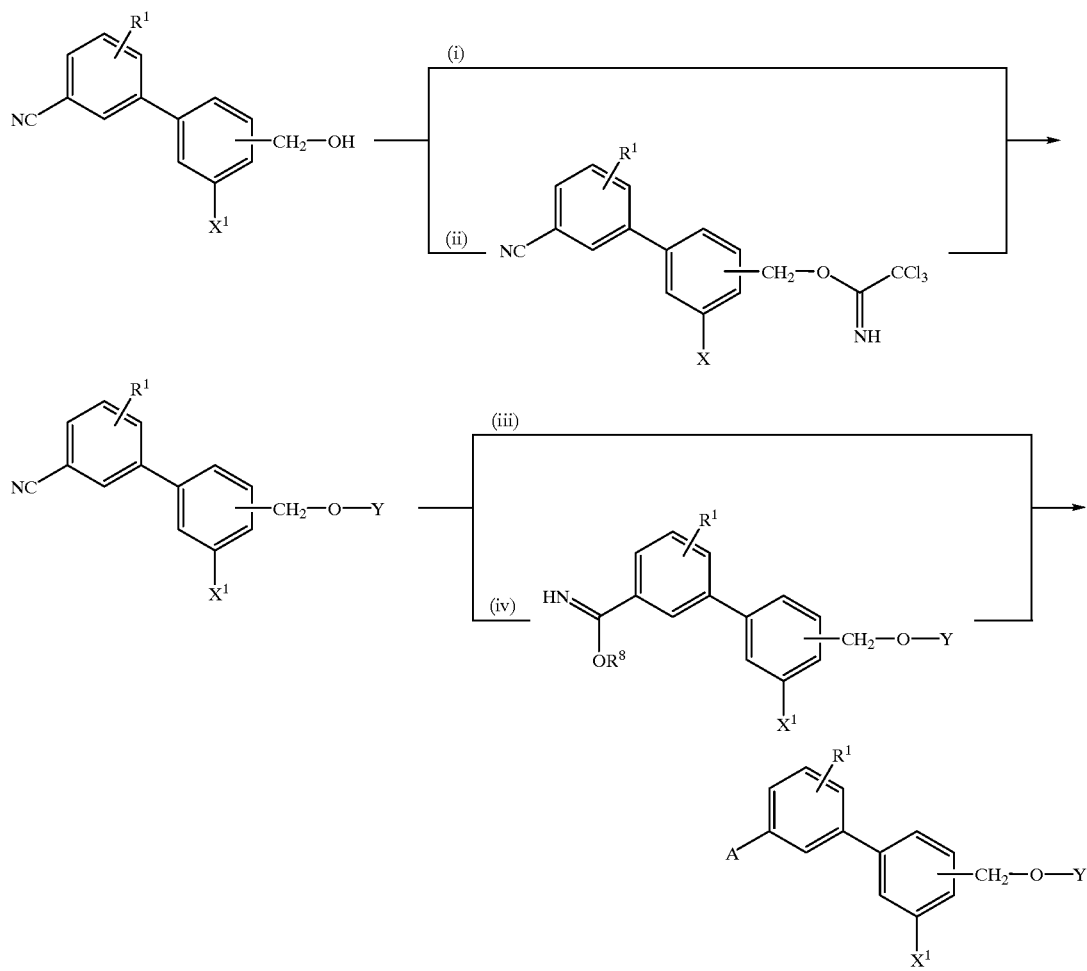

(wherein A, $R^1$, and Y mean the same substituents as the substituents defined in the above-mentioned general formula (1), respectively; $X^1$ means a $C_1$–$C_4$ alkoxycarbonyl group or a hydrogen atom; and $R^8$ means a $C_1$–$C_4$ alkyl group).

Namely, the etherification reaction and the amidination reaction shown in the above-mentioned scheme 1 are carried out by converting the hydroxymethylphenylbenzonitrile compound into the alkoxymethylphenylbenzonitrile compound, for example, by a method shown in the below (i) or (ii), and subsequently applying a subsequently shown treatment (iii) or (iv) to the obtained alkoxymethylphenylbenzonitrile compound. The biphenylamidine derivative which is the compound of the present invention is thus obtained.

(i) The etherification reaction in the presence of a phosphine and an azodicarboxylic acid derivative: the etherification reaction of the hydroxymethylphenylbenzonitrile compound with an alcohol (YOH) is carried out, for example, by a method described in O. Mitsunobu, Synthesis, 1 (1981).

Usually, the reaction proceeds by dissolving the hydroxymethylphenylbenzonitrile compound, which may, if necessary, be protected, in an anhydrous aprotic solvent such as benzene, toluene, THF or an aliphatic ether, adding the alcohol (YOH) to the solution, adding a trialkylphosphine or a triarylphosphine with stirring, and then further adding an azodicarboxylic acid derivative such as diethyl azodicarboxylate (DEAD) or azodicarboxylic acid bisdimethylamide (TMAD). The reaction is usually carried out using tributylphosphine or triphenylphosphine as the phosphine at 0–80° C. for 6–24 hours, preferably at 20–50° C. for 8–16 hours.

(ii) The etherification reaction through a trichloroacetimidate: the etherification reaction of the hydroxymethylphenylbenzonitrile compound (1) with the alcohol (YOH) may be carried out by converting the hydroxymethylphenylbenzonitrile compound, which is protected, if necessary, into the trichloroacetimidate and then reacting the trichloroacetimidate with the alcohol (YOH).

The trichloroacetimidate is obtained by dropwisely adding trichloroacetonitrile to the solution of an alkoxide obtained from the hydroxymethylphenylbenzonitrile compound and a metal hydride such as sodium hydride in an etherial anhydrous solvent in the atmosphere of nitrogen, stirring the mixture for 1–5 hours, adding the solvent mixture of a lower alcohol with a hydrocarbon solvent such as pentane, hexane or heptane, stirring the mixture, filtering off insolubles and then concentrating the filtrate. The alkoxide is usually prepared in THF or diethyl ether at −78 to +30° C., and the reaction of the alkoxide with the trichloroacetonitrile proceeds by stirring at 0–50° C. for 1–12 hours. The reaction is preferably carried out by preparing the alkoxide at −30 to +10° C., dropwisely adding the trichloroacetonitrile and then stirring the reaction solution at 10–40° C. for 2–6 hours.

The alkoxymethylphenylbenzonitrile compound can be synthesized by mixing the obtained trichloroacetimidate with the alcohol (YOH) in the presence of an organic acid such as a sulfonic acid in an aliphatic ether such as diethyl ether or THF and then stirring the mixture at −20 to 40° C. for 6–24 hours. The reaction is carried out by using p-toluene sulfonic acid or trifluoromethane sulfonic acid as the organic acid, starting the reaction at −20 to 0° C., gradually raising the temperature of the reaction solution up to 10–30° C. and simultaneously stirring the reaction solution for 12 to 18 hours.

(iii) The biphenylamidine derivative represented by the general formula (1), wherein $X^1$ is a hydrogen atom, can be synthesized by reacting the alkoxymethylphenylbenzonitrile compound with ammonium chloride in the presence of a trialkylaluminum.

The reaction usually proceeds by mixing the ammonium chloride with the trialkylaluminum, such as trimethylaluminum, triethylaluminum or tributylaluminum, dissolved in an anhydrous hydrocarbon solvent such as pentane or hexane in an anhydrous hydrocarbon solvent such as hexane, benzene or toluene at −10 to 50° C., stirring the mixture for 1–12 hours, adding the alkoxymethylphenylbenzonitrile compound to the mixture at −30 to +30° C. and stirring at 10–100° C. for 6–24 hours. The reaction is preferably carried out by adding the ammonium chloride to benzene or toluene, dropwisely adding the pentane or hexane solution of the trimethylaluminum to the mixture at 0 to +30° C., stirring for 2 to 6 hour, adding the benzene or toluene solution of the alkoxymethylphenylbenzonitrile compound and further stirring at 40 to 80° C. for 12 to 18 hours.

(iv) The biphenylamidine derivative represented by the general formula (1), wherein $X^1$ represents a hydrogen atom or a $C_1$–$C_4$ alkoxycarbonyl group, can be produced by reacting ammonia or one of various kinds of amines with the imidate (5) obtained by reacting the nitrile compound with a $C_1$–$C_4$ alcohol ($R^8$OH) containing hydrogen chloride. For example, the biphenylamidine derivative can be synthesized by the method mentioned in the following (iv-a) or (iv-b).

(iv-a) The amidination reaction through an imidation reaction using the alcohol solution of a hydrogen halide: the reaction for obtaining the imidate from the alkoxymethylphenylbenzonitrile and the alcohol ($R^8$OH) proceeds, for example, by dissolving the alkoxymethylphenylbenzonitrile compound in the $C_1$–$C_4$ alcohol ($R^8$OH) containing a hydrogen halide such as hydrogen chloride or hydrogen bromide and stirring the mixture. The reaction is usually carried out at −20 to 30° C. for 12 to 96 hours. The reaction is preferably carried out at −10 to +30° C. for 24 to 72 hours.

The reaction of the imidate with the ammonia proceeds by stirring the imidate in a $C_1$–$C_4$ alcohol, such as methanol or ethanol, an aliphatic ether, such as diethyl ether, a halogenated hydrocarbon, such as dichloromethane or chloroform, or their mixture solvent which contains the ammonia or an amine, such as hydroxylamine, hydrazine or a carbamate ester, to produce the biphenylamidine derivative which is the compound of the present invention. The reaction is usually carried out at −10 to +50° C. for 1 to 48 hours. The reaction is preferably carried out at 0 to +30° C. for 2 to 12 hours.

(iv-b) The amidination reaction through the imidate prepared, while directly bubbling a hydrogen halide into the reaction solution: the reaction of the alkoxymethylphenylbenzonitrile compound with the alcohol ($R^8$OH) proceeds, for example, by dissolving the alkoxymethylphenylbenzonitrile compound in an aliphatic ether such as diethyl ether, a halogenated hydrocarbon such as chloroform, or an aprotic olvent such as benzene, adding an equivalent or excessive amount of the $C_1$–$C_4$ alcohol ($R^8$OH), blowing a hydrogen halide such as hydrogen chloride or hydrogen bromide in the mixture at −30 to 0° C. for 30 minutes to 6 hours with stirring, stopping the bubbling of the hydrogen halide, and further stirring at 0–50° C. for 3–96 hours. The reaction is preferably carried out by bubbling the hydrogen chloride in the halogenated hydrocarbon containing an equivalent or excessive amount of methanol or ethanol at −10 to 0° C. for 1–3 hours with stirring, stopping the bubbling of the hydrochloride, and further stirring at 10–40° C. for 8–24 hours.

The imidate thus obtained is stirred in a $C_1$–$C_4$ alcohol solvent, such as methanol or ethanol, an aliphatic ether solvent, such as diethyl ether, a halogenated hydrocarbon solvent, such as chloroform, or their mixture solvent which contains ammonia or an amine, such as hydroxylamine, hydrazine or a carbamate ester, thereby capable of being converted into the biphenylamidine derivative which is the compound of the invention. The reaction is usually carried out at −20 to 50° C. for 1 to 48 hours. The reaction is preferably carried out in saturated ammonia ethanol at −0 to +30° C. for 2 to 12 hours.

The compound represented by the general formula (1), wherein X represents a carboxyl group, is produced by hydrolyzing the ester group of the compound having the $C_1$–$C_4$ alkoxycarbonyl group as X, among the biphenylamidine produced according to the above-mentioned (iv).

scheme 2

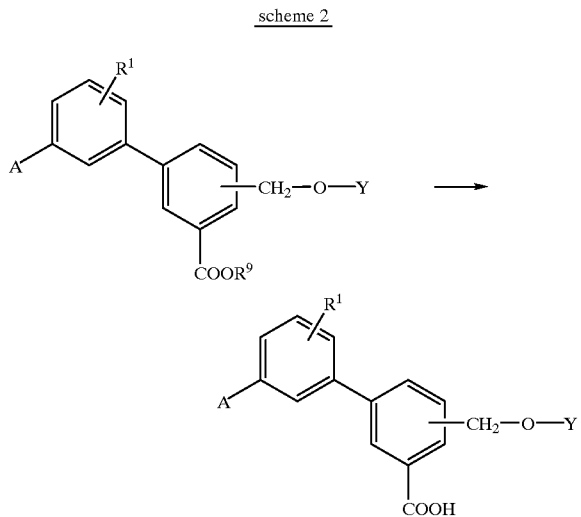

[wherein, A, $R^1$, and Y mean the same substituents as the substituents defined in the above-mentioned general formula (1), respectively ; $R^9$ represents a $C_1$–$C_4$ alkyl group].

Namely, the hydrolysis reaction represented by the above-mentioned scheme 2 may, if necessary, be carried out under a basic condition, an acidic condition or a neutral condition. A base used in the reaction under the basic condition includes sodium hydroxidde, potassium hydroxide, lithium hydroxide and barium hydroxide, and an acid used in the reaction under the acidic condition includes hydrochloric acid, sulfuric acid, Lewis acids such as boron trifluoride, trifluoromethane sulfonic acid and p-toluene sulfonic acid. A substance used in the reaction under the neutral condition includes the alkali metal salts of halide ions, thiol and selenol, such as lithium iodide and lithium bromide, trimethylsilane iodide, and enzymes such as esterases. A solvent used in the reaction includes polar solvents such as water, alcohols, acetone, dioxane, THF, DMF, and DMSO, and their mixtures. The reaction is usually carried out at room temperature or under heating for 2–96 hours. Suitable conditions such as a suitable reaction temperature and a suitable reaction time depend on reaction conditions used in the reaction, and are suitably selected by a conventional method.

And, the compound represented by the general formula (1), wherein $R^5$ represents a hydrogen atom, synthesized by the above-mentioned methods may be reacted with an imidate compound in the presence of a base in a proper solvent to introduce an alkanoylimidoyl group, an arylalkanoylimidoyl group or a benzoylimidoyl group.

scheme 3

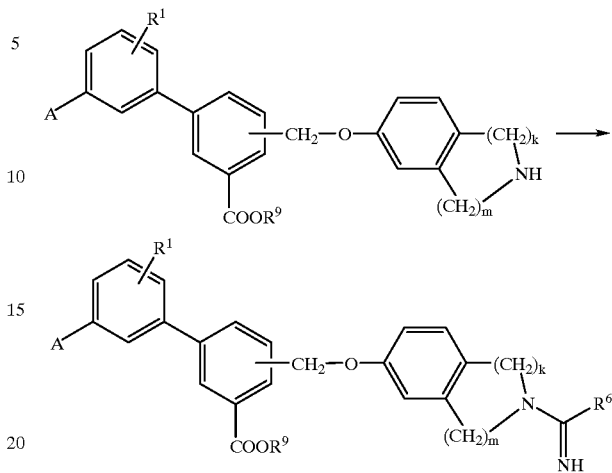

[wherein, A, $R^1$, $R^6$, k, and, m mean the same substituents as the substituents defined in the general formula (1), respectively].

Namely, the imidoylation reaction represented by the above-mentioned scheme 3 proceeds mixing the compound having the secondary amino group with a suitable imidate compound in the presence of a base in water, a $C_1$–$C_4$ alcohol, such as methanol or ethanol, an aliphatic ether, such as diethyl ether, a halogenated hydrocarbon, such as chloroform, a polar solvent, such as DMF or DMSO, or their mixture solvent with stirring. The reaction is usually carried out at room temperature for 1 to 24 hours. The base herein used includes N-methylmorpholine, triethylamine, diisopropylethylamine, sodium hydroxide and potassium hydroxide.

The carboxyl group of the compound of the general formula (1), wherein the substituent X represents the carboxyl group, may be converted into various kinds of ester groups by the following methods (viii), (ix), and (x).

(viii) The conversion of the carboxyl group into an alkoxycarbonyl group: the compound of the formula (1), wherein the substituent X represents the carboxyl group, is reacted with an equivalent or excessive amount of an alkylating agent (for example, an acyloxymethyl chloride such as acetoxymethyl chloride or pivaloyloxymethyl chloride, an allyl chloride compound, or a benzyl chloride compound) in the presence of a tertiary amine such as triethylamine or diisopropylethylamine in a halogenated hydrocarbon such as dichloromethane, an aliphatic ether such as THF, an aprotic polar solvent such as DMF, or their mixture solvent, at −10 to +80° C., whereby the carboxyl group can be converted into the alkoxycarbonyl group. The conversion reaction is preferably carried out using an equivalent or slightly excessive amount of the alkylating agent in the presence of diisopropylethylamine at 20–60° C. for 2–24 hours.

(ix) The conversion of the carboxyl group into an aralkoxycarbonyl group: the compound represented by the general formula (1), wherein the substituent X represents the carboxyl group, is reacted with an equivalent or excessive amount of an alcohol such as benzyl alcohol in the presence of an acid catalyst such as hydrogen chloride, sulfuric acid or a sulfonic acid in a halogenated hydrocarbon such as dichloromethane as a solvent, whereby the carboxyl group can be converted into the aralkoxycarbonyl group. The reaction is usually carried out at room temperature or under heating for 1–72 hours. The reaction is preferably carried out using an equivalent or slightly excessive amount of the alcohol in the presence of diisopropylethylamine at 20 to 60° C. for 2 to 24 hours.

(x) The conversion of the carboxyl group into an aryloxycarbonyl group: the compound represented by the formula (1), wherein the substituent X represents the carboxyl group, is reacted with an equivalent or excessive amount of an aromatic compound having a hydroxyl group, such as phenol, in the presence of a condensing agent such as dicyclohexylcarbodiimide in an aliphatic ether such as diethyl ether as a solvent, whereby the carboxyl group can be converted into the aryloxycarbonyl group. The reaction is usually carried out at 0 to 50° C. for 1–48 hours. The reaction is preferably carried out at room temperature for 3–24 hours.

Further, the compound represented by the general formula (1) can be produced by arbitrarily combining processes capable of being adopted by those skilled in the art, such as other known etherification, amidination, hydrolysis, and alkylimidoylation processes.

The above produced biphenylamidine derivative represented by the general formula (1) can be isolated or purified by a known method, such as extraction, precipitation, fractional chromatography, fractional crystallization or recrystallization. The pharmaceutically acceptable salt of the compound of the present invention can be produced by the application of an ordinary salt-forming reaction.

EXAMPLES

The present invention will be explained in more detail by, but it is by no means limited to, the following production examples, examples, and test examples.

[Production Example 1]

3-Amino-5-hydroxymethylbenzoic acid methyl ester

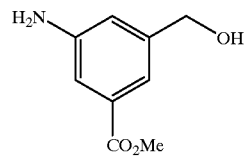

85 g of 3-nitro-5-methoxycarbonylbenzoic acid was dissolved in 200 ml of THF under the flow of nitrogen, cooled with ice, stirred, and simultaneously mixed with 43.4 ml of borane dimethyl sulfide complex.

After stirred for 18 hours, the solution was mixed with 200 ml of water and 96 g of potassium carbonate, and then extracted with ethyl acetate. The obtained organic layer was washed with an aqueous solution of sodium chloride, and then dried over magnesium sulfate. The obtained solid matter was dissolved in 800 ml of ethyl acetate, mixed with 750 mg of 10% Pd/C and then stirred under the flow of hydrogen. After the reaction was finished, the reaction solution was filtered and concentrated to obtain 64 g of the title compound.

$^1$H NMR (270 MHz): δ (CDCl$_3$) 7.39 (s, 1H), 7.26(s, 1H), 6.89(s, 1H), 4.64(s, 1H), 3.89(s, 3H), 2.30(s, 1H).

[Production Example 2]

5-Hydroxymethyl-3-iodobenzoic acid methyl ester

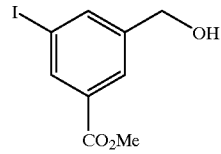

34.3 g of the 3-mino-5-hydroxymethylbenzoic acid methyl ester obtained in the production example 1 was dissolved in 200 ml of THF, cooled with ice, stirred, and simultaneously mixed with 75 g of hydroiodic acid. While stirred, the obtained solution was mixed with 100 ml of an aqueous solution of 13.73 g of sodium nitrite. The obtained mixture was stirred at 0° C. for 40 min and then mixed with 150 ml of an aqueous solution of 34.6 g of potassium iodide. The mixture was stirred at 40° C. for 2 hours, mixed with 300 ml of water, concentrated, and then extracted with ethyl acetate. The obtained organic layer was washed with an aqueous solution of sodium chloride, dried over sodium sulfate and then purified by silica gel chromatography to obtain 23.1 g (42%) of the title compound.

$^1$H NMR (270 MHz): δ (CDCl$_3$) 8.29(s, 1H), 7.98(s, 1H), 7.93(s, 1H), 4.72(d, 1H, J=5, 6 Hz), 3.92(s, 3H), 1.81(t, 1H, J=5.6 Hz).

[Production Example 3]

Dihydroxy-(3-cyanophenyl)borane

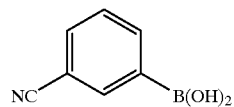

20 g of 3-bromobenzonitrile was dissolved in 100 ml of dry THF, and then mixed with 37.6 ml of triisopropoxyborane in the atmosphere of nitrogen. The solution was cooled at −78° C., and then 98.3 ml of a 1.6M n-butyl lithium hexane solution was dropwisely added to the cooled solution for about 30 minutes with stirring. The mixture was stirred at room temperature for 30 minutes, cooled at 0° C. and mixed with 220 ml of 4M sulfuric acid. The solution was heated and refluxed overnight, again cooled at 0° C., mixed with 340 ml of a 5M aqueous solution of sodium hydroxide, and then extracted with 200 ml of diethyl ether. The aqueous phase was separated, mixed with 6M hydrochloric acid until to give pH 2, and then twice extracted with 300 ml of ethyl acetate. The obtained ethyl acetate layer was dried over MgSO$_4$, and the solvent was distilled away. The obtained crude product was recrystallized from DMF-water to obtain 11.6 g (72%) of the title compound as needle-like pale yellow crystals.

$^1$H NMR (270 MHz): δ (DMSO-d6) 8.5(brs, 2H), 8.3–7.6 (m, 4H).

[Production Example 4]

3-(3-cyanophenyl)-5-(hydroxymethyl)benzoic acid methyl ester

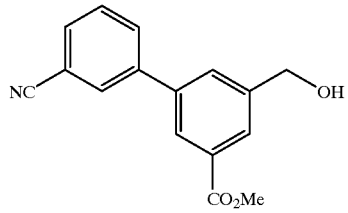

3.08 g of the 5-hydroxymethyl-3-iodobenzoic acid methyl ester obtained in the production example 2 was dissolved in 50 ml of dry DMF under the flow of nitrogen and then mixed with 2.32 g of the compound in the production example 3, 2.18 g of potassium carbonate and 456 mg of tetrakis (triphenylphosphine) palladium (0). The obtained mixture solution was heated and stirred at 90° C. overnight, mixed with water to stop the reaction, and then extracted with ethyl acetate. The obtained ethyl acetate layer was dried over $MgSO_4$, and the solvent was distilled away. The residue was purified by silica gel column chromatography to obtain 2.05 g (73%) of the title compound. Colorless crystals.

$^1$H NMR (270 MHz): δ (CDCl$_3$) 8.2–7.5(m, 7H, Ar-H), 4.84(d, J=3.7 Hz, 2H), 3.96(s, 3H), 2.1(brs, 1H).

[Production Example 5]

3-(3-cyanophenyl)-5-(phenoxymethyl)benzoic acid methyl ester

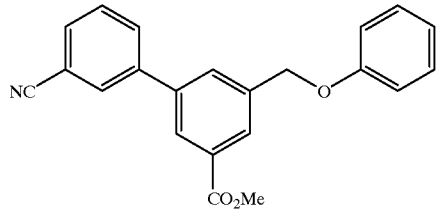

30 mg of the 3-(3-cyanophenyl)-5-(hydroxymethyl) benzoic acid methyl ester produced in the production example 4 was dissolved in dry THF in the atmosphere of nitrogen, mixed with 10.5 mg of phenol, 35.4 mg of triphenylphosphine and 21 μl of azodicarboxylic acid diethyl ester at room temperature, and then stirred at room temperature overnight. The solvent was distilled away, and the residue was purified by silica gel chromatography to obtain 31 mg (77%) of the title compound (colorless, crystal).

$^1$H NMR (270 MHz): δ (CDCl$_3$) 8.2–7.5(m, 7H), 7.4–7.0 (m, 5H), 5.17(s, 2H), 3.97(s, 3H).

[Example 1]

3-(3-amidinophenyl)-5-(phenoxymethyl)benzoic acid methyl ester.

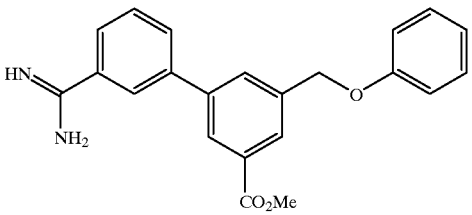

45 mg of the compound in the production example 5 was dissolved in a saturated HCl ethanol solution and stirred at room temperature for 2 days. The solvent was distilled away, and the residue was mixed with a saturated ammonia ethanol solution and further stirred at room temperature overnight. The solvent was distilled away, and the residue was fractionated and purified by HPLC to obtain 20 mg (yield: 33%) of the title compound (colorless, solid).

$^1$H NMR (270 MHz): δ (CDCl$_3$) 8.2–6.9(m, 12H), 5.24(s, 2H), 3.96(s, 3H)

[Example 2]

3-(3-amidinophenyl)-5-(phenoxymethyl)benzoic acid

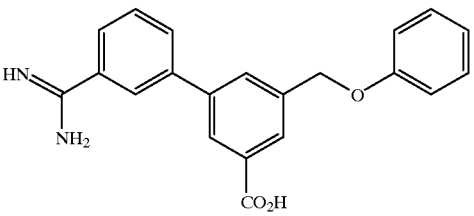

10 mg of the compound obtained in the example 1 was mixed with 2N hydrochloric acid (2 ml) and stirred at 80° C. for 2 days. The solvent was distilled away, and the residue was fractionated and purified by HPLC to obtain 4.8 mg (yield: 50%) of the title compound (colorless, solid).

$^1$H NMR (270 MHz): δ (CDCl$_3$) 8.2–6.8(m, 12H), 5.22(s, 2H)

[Production Example 6]

3-(3-cyanophenyl)-5-((4-methylethyl)phenoxymethyl) benzoic acid methyl ester

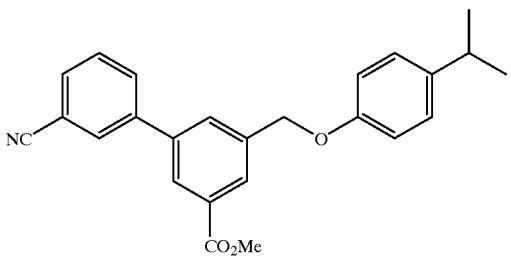

The production reaction was carried out by a method similar to the method in the production example 5, while 4-methylethylphenol was added instead of the phenol. 33 mg (yield: 38%) of the purified title compound was obtained.

$^1$H NMR (270 MHz): δ (CDCl$_3$) 8.2–7.5(m, 7H), 7.16(d, J=8.6 Hz), 6.93(d, J=8.6 Hz), 5.15(s, 21), 3,97(s, 3H), 2.87(sept, J=7, 1H), 1.23(d, J=7, 6H)

[Example 3]
3-(3-amidinophenyl)-5-((4-methylethyl)phenoxymethyl) benzoic acid methyl ester

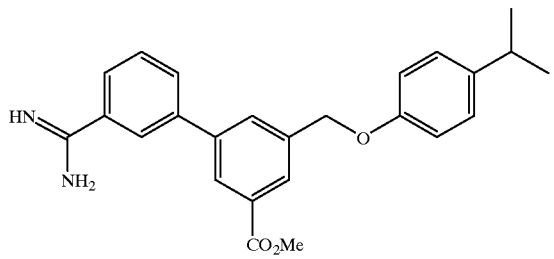

The compound obtained in the production example 6 was used by a method similar to the method in the example 1 to obtain 18 mg (yield: 41%) of the title compound.

$^1$H NMR (270 MHz): δ (CDCl$_3$) 8.2–7.5(m, 7H), 7.17(d, J=9 Hz), 6.93(d, J=9 Hz), 5.21(s, 2H), 3.98(s, 3H), 2.85(sept, J=7 Hz, 1H), 1.24(d, J=Hz7, 6H)

[Example 4]
3-(3-amidinophenyl)-5-((4-methylethyl)phenoxymethyl) benzoic acid

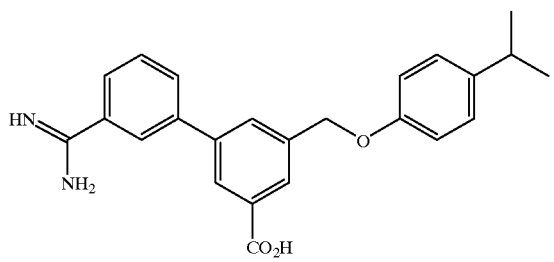

The compound obtained in the example 3 was used by a method similar to the method in the example 2 to obtain 5 mg (yield: 40%) of the title compound. Colorless solid.

$^1$H NMR (270 MHz): δ (CDCl$_3$) 8.3–7.7(m, 7H), 7.17(d, J=9 Hz), 6.93(d, J=9 Hz), 5.21(s, 2H), 2.85(sept, J=7 Hz, 1H), 1.24(d, J=7 Hz, 6H)

[Production Example 7]
3-(3-cyanophenyl)-5-((3-(2,2,2-trifluoroacetylamino) methyl)phenoxymethyl) benzoic acid methyl ester

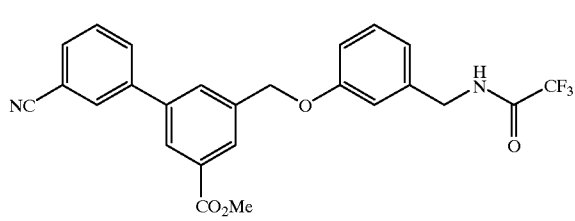

The production reaction was carried out by a method similar to the method in the production example 5, while 3-(2,2,2-trifluoroacetylamino)methylphenol was added instead of the phenol. 88 mg (yield: 84%) of the title compound was obtained.

$^1$H NMR (270 MHz): δ (CDCl$_3$) 8.2–7.5(m, 7H), 7.4–7.0 (m, 4H), 5.18(s, 2H), 4.52(d, J=6, 2H), 3.98(s, 3H).

[Example 5]

3-(3-amidinophenyl)-5-((3-(aminomethyl)phenoxy)methyl) benzoic acid methyl ester

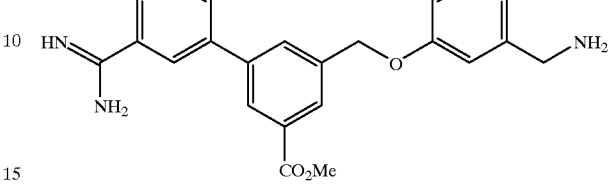

80 mg of the compound obtained in the production example 7 was dissolved in 10 ml of methylene chloride, and mixed with 0.1 ml of methanol. Hydrogen chloride was bubbled into the solution at 0° C. for one hour. The reaction vessel was stoppered, and the solution was stirred overnight, followed by distiing away the solvent. 6 ml of a saturated ammonia ethanol solution was added to the obtained solid and then stirred at room temperature for 8 hours. After the solvent was distilled away, the residue was mixed with 2 ml of methanol and 1 ml of a 1M aqueous solution of sodium carbonate, and stirred at room temperature overnight. The solution was neutralized with diluted hydrochloric acid, and the solvent was distilled away. The residue was fractionated and purified by reversed phase chromatography to obtain 5 mg (yield: 5%) of the title compound.

$^1$H NMR (270 MHz): δ (DMSO-d6) 8.4–7.0(m, 11H), 5.29(s, 21), 4.02(brs, 2H), 3.92(s, 3H).

[Example 6]

3-(3-amidinophenyl)-5-((3-(aminomethyl)phenoxy)methyl) benzoic acid

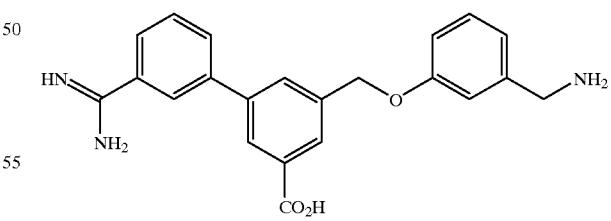

The compound obtained in the example 5 was used by a method similar to the method in the example 2 to obtain 5 mg (yield: 45%) of the title compound. White solid.

$^1$H NMR (270 MHz): δ (CD3DC) 8.4–7.0(m, 11H), 5.28(m, 2H), 4.09(brs, 2H).

[Production Example 8]
3-(3-cyanophenyl)-5-((5-chloro-4-methyl-2-(2,2,2-trifluoroacetylamino)-phenoxy)methyl)benzoic acid methyl ester

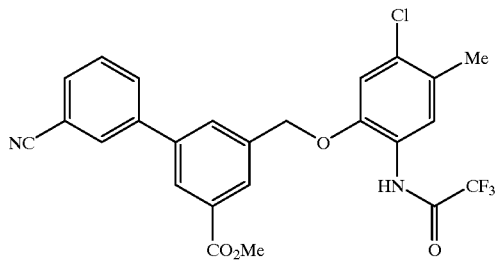

The production reaction was carried out by a method similar to the method in the production example 5, while 5-chloro-4-methyl-2-(2,2,2-trifluoroacetylamino)-phenol was added in stead of the phenol. 68 mg (yield: 36%) of the title compound was obtained.

$^1$H NMR (270 MHz): δ (CDCl$_3$) 8.2–7.0(m, 9H), 5.24(m, 2H), 3.99(s, 3H), 2.35(s, 3H).

[Example 7]
3-(3-amidinophenyl)-5-((2-amino-5-chloro-4-methylphenoxy)methyl)benzoic acid methyl ester

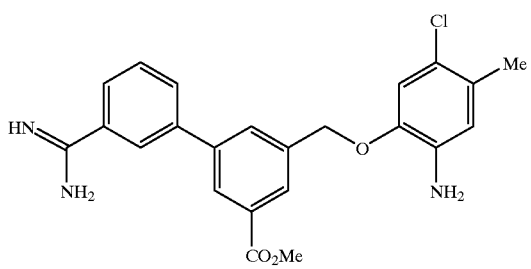

The compound obtained in the production example 8 was used and reacted similarly as in the example 5 to obtain 3.5 mg (5%) of the title compound.

$^1$H NMR (270 MHz): δ (DMSO-d6) 8.4–7.7(m, 7H), 6.96(s, 1H), 6.61(s, 1H), 5.25(s, 2H), 3.92(s, 3H), 2.13(s, 3H).

[Example 8]
3-(3-amidinophenyl)-5-((2-amino-5-chloro-4-methylphenoxy)methyl)benzoic acid

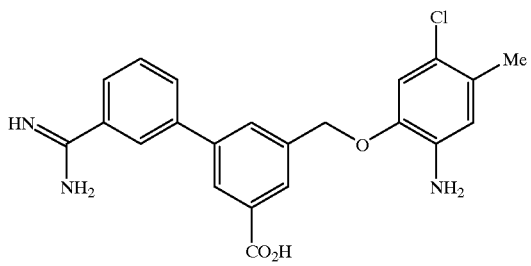

The compound obtained in the example 7 was used and reacted similarly as in the example 2 to obtain 1.40 mg (yield: 10%) of the title compound.

$^1$H NMR (270 MHz): δ (DMSO-d6) 8.3–7.7(m, 7H), 6.96(s, 1H), 6.62(s, 1H), 5.25(s, 2H), 2.14(s, 3H).

[Production Example 9]
2,2,2-trifluoro-N-(2-(3-methoxyphenyl)ethyl)ethanamide

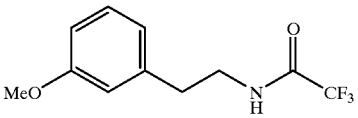

2.0 g of 3-methoxyphenylethylamine was dissolved in DMF. While the solution was cooled at 0° C., 2.24 ml of trifluoroacetic anhydride was dropwisely added to the solution in the atmosphere of nitrogen. The mixture was further mixed with 2.0 ml of triethylamine, returned to room temperature and then as such stirred overnight. The obtained solution was poured on the cooled mixture of a saturated aqueous solution of sodium bicarbonate with ethyl acetate to stop the reaction. The obtained organic layer was separated, washed with a saturated aqueous solution of ammonium chloride and with a saturated aqueous solution of sodium chloride, and dried over sodium sulfate. The solvent was distilled away from the solution. The residue was purified by silica gel chromatography to obtain 2.97 g (yield: 91%) of the title compound.

$^1$H NMR (270 MHz): δ (CDCl$^3$-D$_2$O) 7.3–6.6(m, 4H), 3.97(s, 3H), 3.62(t, J=7 Hz, 2H), 2.86(t, J=7 Hz, 2H).

[Production Example 10]
2,2,2-trifluoro-N-(2-(3-hydroxyphenyl)ethyl)ethanamide

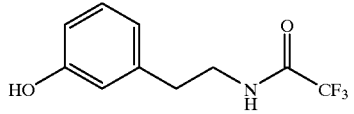

891 mg of the compound obtained in the production example 9 was dissolved in 10 ml of dichloromethane. The obtained solution was mixed with 2.5 g of aluminum chloride, and stirred at room temperature for five days. The solvent was distilled away, and the residue was mixed with 3 ml of ethanethiol and stirred at room temperature overnight. The solvent was distilled away, and the residue was mixed with cooled diluted hydrochloric acid and ethyl acetate. The organic layer was separated, washed with an aqueous solution of sodium bicarbonate and dried over magnesium sulfate. The solvent was distilled away. The residue was purified by silica gel chromatography to obtain 549 mg (65%) of the title compound.

$^1$H NMR (270 MHz): δ (CDCl$_3$-D$_2$O) 7.3–6.6(m, 4H), 3.62(t, J=7 Hz, 2H), 2.86(t, J=7 Hz, 2H).

[Production example 11]
3-(3-cyanophenyl)-5-(3-(2-(2,2,2-trifluoroacetylamino)ethyl)phenoxymethyl) benzoic acid methyl ester

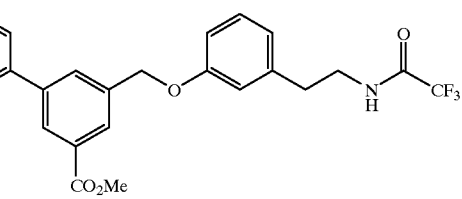

110 mg of triphenylphosphine was dissolved in 5 ml of N-methylphosphine in the atmosphere of nitrogen, and 178

μl of DEAD was dropwisely dropped on the solution at 0° C. The obtained solution was mixed with 61 mg of (2,2,2-trifluoro-N-(2-(3-hydroxyphenyl)ethyl)ethanamide and 70 mg of 3-(3-cyanophenyl)-5-(hydroxymethyl)benzoic acid methyl ester, stirred at room temperature overnight and then poured on an aqueous solution of ammonium chloride to stop the reaction. The solution was extracted with ethyl acetate, and the obtained organic layer was dried. The solvent was distilled away, and the residue was purified by silica gel chromatography to obtain 79 mg (62.5%) of the title compound. Colorless solid.

¹HNMR (270 MHz): δ (CDCl₃) 8.2–6.8(m, 11H), 5.15(s, 2H), 3.97(s, 3H), 3.62(dt, J=7 Hz, 7 Hz, 2H), 2.89(t, J=7 Hz, 2H).

[Example 9]

3-(3-amidinophenyl)-5-((3-amino-2-ethyl)phenoxymethyl) benzoic acid methyl ester

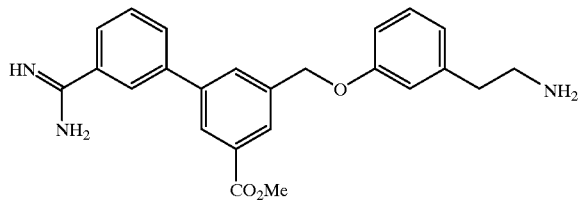

70 mg of the compound obtained in the production example 11 was used and reacted similarly as in the example 5 to obtain 16.2 mg of the title compound. Colorless solid.

¹H NMR (270 MHz): δ (DMSO-d6) 8.3–6.7(m, 11H), 5.22(s, 2H), 3.88(s, 3H), 2.89(t, J=7.4 Hz, 2H), 2.73(t, J=7.4 Hz, 2H).

[Example 10]

3-(3-amidinophenyl)-5-((3-amino-2-ethyl)phenoxymethyl) benzoic acid

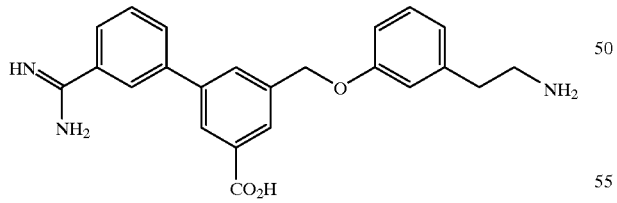

10 mg of the compound obtained in the example 9 was further mixed with 1 ml of a 1M aqueous solution of sodium carbonate, stirred at room temperature overnight and then neutralized with diluted hydrochloric acid. The solvent was distilled away, and the residue was purified by HPLC to obtain 3.2 mg of the title compound. Colorless solid.

¹H NMR (270 MHz): δ (DMSO-d6) 8.4–6.8(m, 11H), 5.19(s, 2H), 2.91(t, J=7.8 Hz, 2H), 2.74(t, J=7.8 Hz, 2H).

[Production Example 12]

3-(3-cyanophenyl)-5-((2-amino(3-pyridyloxy))methyl) benzoic acid methyl ester

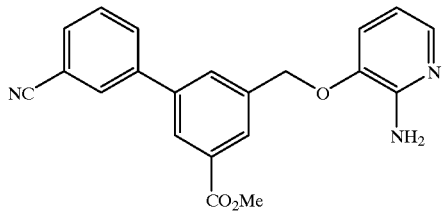

100 mg of 3-(3-cyanophenyl)-5-(hydroxymethyl)benzoic acid methyl ester produced in the production example 4 was dissolved in dry benzene in the atmosphere of nitrogen. The solution was mixed with 62 mg of 2-amino-3-hydroxypyridine at room temperature, further mixed with 138 μl mg of tributylphosphine and 97 mg of azodicarboxylic acid bisdimethylamide: TMAD with stirring, and stirred at room temperature overnight. The solvent was distilled away, and the residue was purified by silica gel chromatography to obtain 50 mg (39%) of the title compound (colorless, crystal).

¹H NMR (270 MHz): δ (CDCl₃) 8.3–7.5(m, 8H), 6.99(t, J=8 Hz, 1H), 6.6(m, 1H), 5.18(s, 2H), 3.97(s, 3H).

[Example 11]

3-(3-amidinophenyl)-5-((2-amino(3-pyridyloxy))methyl) benzoic acid methyl ester

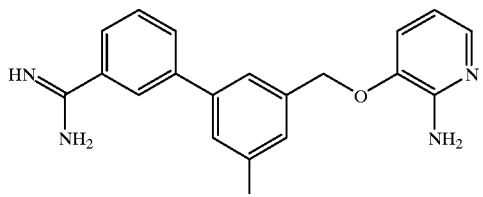

45 mg of the compound obtained in the production example 12 was dissolved in 10 ml of methylene chloride, and mixed with 0.1 ml of methanol. Hydrogen chloride was blown in the solution at 0° C. for 1 hour. The reaction vessel was stoppered, and the solution was stirred overnight. The solvent was distilled away. The obtained solid residue was mixed with 10 ml of a saturated ammonia ethanol solution and stirred at room temperature for 8 hours. The solvent was distilled away, and the residue was fractionated and purified by HPLC to obtain 19 mg (40%) of the title compound. Colorless solid.

¹H NMR (270 MHz): δ (DMSO-d6) 8.4–7.5(m, 9H), 6.8(m, 1H), 5.43(s, 2H), 3.92(s, 3H).

[Production Example 13]

3-(3-cyanophenyl)-5-((2-amino-4-methylphenoxy)methyl) benzoic acid methyl ester

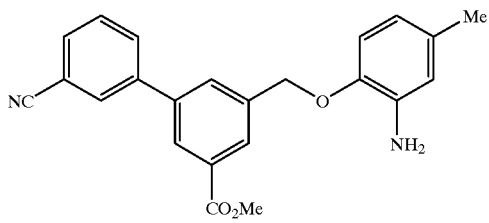

2-amino-4-methylphenol was used instead of the 2-amino-3-hydroxypyridine by a method similar to the method in the production example 2 to obtain 120 mg (quant.) of the title compound.

$^1$H NMR (270 MHz): δ (CDCl$_3$) 8.2–7.5(m, 7H), 6.8–6.5 (m, 3H), 5.16(s, 2H), 3.97(s, 3H), 2.23(s, 3H).

[Example 12]

3-(3-amidinophenyl)-5-((2-amino-4-methylphenoxy) methyl)benzoic acid methyl ester

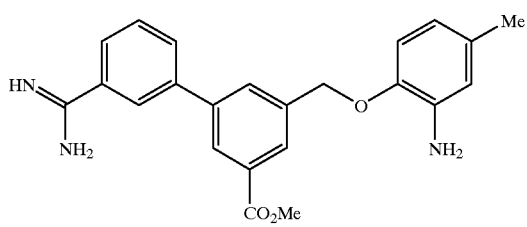

The compound obtained in the production example 13 was used and reacted similarly as in the example 11 to obtain 10 mg (9%) of the title compound. Colorless solid.

$^1$H NMR (270 MHz): δ (DMSO-d6) 8.4–7.7(m, 7H), 6.9–6.5(m, 3H), 5.24(s, 2H), 3.92(s, 3H), 2.15(s, 3H).

[Production Example 14]

3-(3-cyanophenyl)-5-(3-aminophenoxymethyl)benzoic acid methyl ester

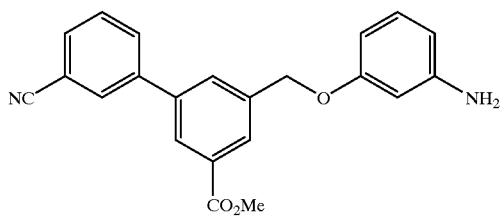

3-aminophenol was used and reacted instead of the 2-amino-3-hydroxypyridine by a method similar to the method in the production example 12 to obtain 58 mg of the title compound. Yield: 40%.

$^1$H NMR (270 MHz): δ (CDCl$_3$) 8.2(s, 1H), 8.1(s, 1H), 7.8–7.9(m, 3H), 7.65(d, 1H), 7.55(t, 1H), 6.95–7.10(m, 1H), 6.15–6.45(m, 3H), 5.12(s, 2H), 3.95(s, 3H), 4.2–3.5(bs, 2H).

[Example 13]

3-(3-amidinophenyl)-5-(3-aminophenoxymethyl)benzoic acid methyl ester

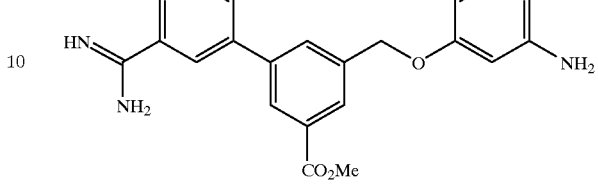

The compound obtained in the production example 14 was used and reacted similarly as in the production example 11 to obtain 18 mg of the title compound. Yield: 30%.

MS: m/Z 376 [(M+H)$^+$]

[Production Example 15]

3-(3-cyanophenyl)-5-((4-ethyl-3-hydroxyphenoxy)methyl) benzoic acid methyl ester

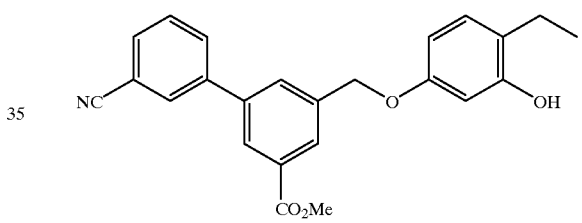

125 mg of triphenylphosphine was dissolved in 10 ml of N-methylmorpholine in the atmosphere of nitrogen, and 203 μl of DEAD was dropwisely added to the solution. The obtained solution was mixed with 76 mg of 4-ethyl-3-(tert-butyldimethylsilyloxy)phenol and 80 mg of 3-(3-cyanophenyl)-5-(hydroxymethyl)benzoic acid methyl ester, stirred at room temperature overnight, and then poured into an aqueous solution of ammonium chloride to stop the reaction. The solution was extracted with ethyl acetate, and the obtained organic layer was dried. The solvent was distilled away, and the residue was purified by silica gel chromatography.

The obtained silyl compound was dissolved in 10 ml of methanol, mixed with 100 mg of potassium fluoride, stirred overnight, poured into a mixture liquid of ethyl acetate with water, and extracted with the ethyl acetate. The obtained organic layer was dried over magnesium sulfate, and the solvent was distilled away. The residue was purified by silica gel chromatography (ethyl acetate: hexane) to obtain 53 mg (37%) of the title compound.

$^1$H NMR (270 MHz): δ (CDCl$_3$) 8.2–7.5(m, 7H), 7.03(d, J=8.4 Hz, 1H), 6.5(m, 2H), 5.09(s, 2H), 3.96(s, 3H), 2.57(q, J=7.5 Hz, 2H), 1.20(t, J=7.5 Hz, 3H).

[Example 14]
3-(3-amidinophenyl)-5-((4-ethyl-3-hydroxyphenoxy)methyl)benzoic acid methyl ester

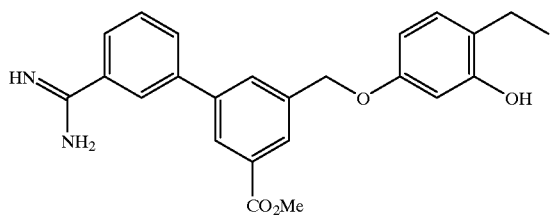

The compound obtained in the production example 15 was used by a method similar to the method in the example 11 to obtain 16 mg (29%) of the title compound. Colorless solid.

$^1$H NMR (270 MHz): δ (DMSO-d6) 8.2–7.6(m, 7H), 6.94(d, J=8.1 Hz, 1H), 6.45(m, 2H), 5.17(m, 2H), 3.91(s, 3H, OCH3), 2.45(q, J=7.3 Hz, 2H), 1.08(t, J=7.3 Hz, 3H).

[Production Example 16]
3-t-butyldimethylsilyloxybenzoic acid methyl ester

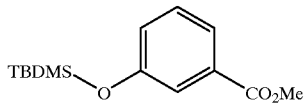

1.53 g of 3-hydroxybenzoic acid methyl ester and 1.69 g of imidazole were placed in a 50 ml flask, and a gas in the reaction system was replaced with nitrogen. 5 ml of DMF was added into the flask and stirred at 0° C. The obtained solution was mixed with 1.57 g of t-butyldimethylsilyl chloride, heated up to room temperature, simultaneously stirred overnight, and then mixed with a saturated aqueous solution of ammonium chloride to stop the reaction. The reaction solution was extracted with diethyl ether, and the obtained organic layer was sequentially washed with water, a saturated aqueous solution of potassium hydrogen sulfate and a saturated aqueous solution of sodium chloride and then dried over magnesium sulfate. The solvent was distilled away under reduced pressure to obtain 1.69 g of the title compound. Yield: 98%.

$^1$H NMR: δ (CDCl$_3$) 7.64(d, 1H), 7.49(s, 1H), 7.29(t, 1H), 7.29(t, 1H), 7.03(q, 1H), 3.91(s, 3H), 0.99(s, 9H), 0.21(s, 6H).

[Production Example 17]
3-t-butyldimethylsilyloxybenzyl alcohol

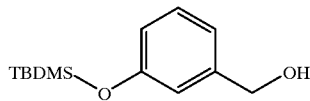

563 mg of lithium aluminum hydride was placed in a 100 ml flask, and a gas in the reaction system was replaced with nitrogen. 30 ml of diethyl ether was added into the flask and stirred at 0° C. The obtained solution was mixed with a solution which was prepared by dissolving 2.63 g of the compound obtained in the production example 16 in 30 ml of diethyl ether, and then stirred at 0° C. for 30 minutes. 1.5 ml of water was dropwisely added to the solution to stop the reaction. The solution was further mixed with about 50 ml of a saturated aqueous solution of sodium sulfate, and the upper organic layer was fractionated. The solvent was distilled away under reduced pressure to obtain 1.69 g of the title compound. Yield: 72%.

$^1$H NMR: δ (CDCl$_3$) 7.21(t, 1H), 6.94(d, 1H), 6.86(s, 1H), 6.76(q, 1H), 4.64(d, 2H), 0.99(s, 9H), 0.20(s, 6H)

[Production Example 18]
3-(t-butyldimethylsilyloxy)phenylmethyl acetate

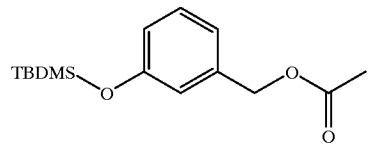

1.69 g of the compound obtained in the production example 17 was placed in a 200 ml flask, and a gas in the reaction system was replaced with nitrogen. 20 ml of dichloromethane and 1.1 ml of pyridine were added into the flask and stirred at 0° C. 1.0 ml of acetyl chloride was dropwisely added to the obtained solution. While being heated up to room temperature, the solution was stirred overnight. Water was added to the solution to stop the reaction. The solution was extracted with diethyl ether. The organic layer was separated, sequentially washed with water, a saturated aqueous solution of potassium hydrogen sulfate, and a saturated aqueous solution of sodium chloride, and then dried over magnesium sulfate. The solvent was distilled away under reduced pressure to obtain 1.92 g of the title compound. Yield: 96%.

$^1$H NMR: δ (CDCl$_3$) 7.23(q, 1H), 6.94(d, 1H), 6.83–6.77 (m, 2H), 5.05(s, 1H), 2.11(s, 3H), 0.98(s, 9H), 0.20(s, 6H)

[Production Example 19]
3-hydroxyphenylmethyl acetate

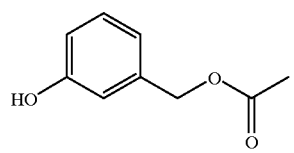

1.92 g of the compound obtained in the production example 18 was placed in a 200 ml flask, and 15 ml of acetonitrile was added into the flask, and stirred at 0° C. The obtained solution was mixed with 1.92 g of lithium boron tetrafluoride and further with a solution which was obtained by dissolving 0.42 ml of concentrated sulfuric acid in 5 ml of acetonitrile, and then stirred at room temperature overnight. The solvent was distilled away under reduced pressure, mixed with water and then extracted with ethyl acetate. The obtained organic layer was washed with water and a saturated aqueous solution of sodium chloride, and dried over magnesium sulfate. The solvent was distilled away under reduced pressure to obtain 1.10 g of the crude product. The obtained crude product was purified by silica gel column chromatography to obtain 989 mg of the title compound. Yield: 88%.

$^1$H NMR: δ (CDCl$_3$) 7.23(t, 1H), 6.93(d, 1H), 6.88–6.75 (m, 2H), 5.22(d, 1H), 5.05(s, 2H), 2.12(s, 3H).

[Production Example 20]

(3-((3-cyanophenyl)-5-(methoxycarbonyl)phenyl)methoxy)phenyl)methyl acetate

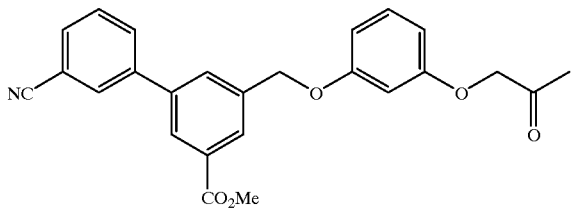

The 3-acetoxymethylphenol obtained in the production example 19 was used and reacted by a method similar to the method in the production example 12 to obtain 126 mg of the title compound. Yield: 76%.

$^1$H NMR: δ (CDCl$_3$) 8.20(s, 1H), 8.13(s, 1H), 7.95–7.85 (m, 3H), 7.68(d, 1H), 7.58(t, 1H), 7.29(t, 1H), 7.05"6.90(m, 3H), 5.18(s, 2H), 5.05(s, 2H), 3.95(s, 3H), 2.12(s, 3H).

[Production Example 21]

3-(3-cyanophenyl)-5-((3-hydroxymethyl)phenyl)methylbenzoic acid methyl ester

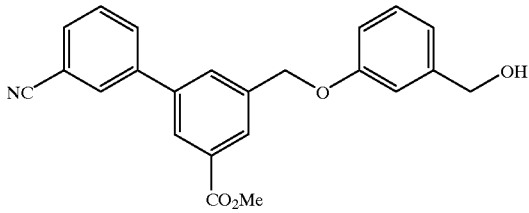

126 mg of the compound obtained in the production example 20 was placed in a 25 ml flask, and 2 ml of THF was added into the flask and stirred at 0° C. The obtained solution was mixed 0.33 ml of a 1 N aqueous solution of sodium hydroxide, stirred at 0° C., further mixed with 0.066 ml of a 5 N aqueous solution of sodium hydroxide and 3 ml of methanol, and then stirred at 0° C. After the finish of the reaction was confirmed by TLC, and 0.66 ml of a 1 N aqueous solution of hydrochloric acid was added. The solvent was distilled away under reduced pressure, and the residue was mixed with water, and then extracted with ethyl acetate three times. The obtained organic layer was washed with a saturated aqueous solution of sodium chloride and dried over magnesium sulfate. The solvent was distilled away under reduced pressure to obtain 114 mg of the title compound (crude product). Yield: 98%.

$^1$H NMR: δ (CDCl$_3$) 8.20(s, 1H), 8.10(s, 1H), 7.80–7.95 (m, 31), 7.68(d, 1H), 7.58(t, 1H), 7.30(s, 1H), 7.05(s, 1H), 6.90–7.00(m, 2H), 5.20(s, 2H), 4.70(s, 2H), 3.95(s, 3H).

[Example 15]

3-(3-amidinophenyl)-5-((3-hydroxymethyl)phenoxymethyl)benzoic acid methyl ester

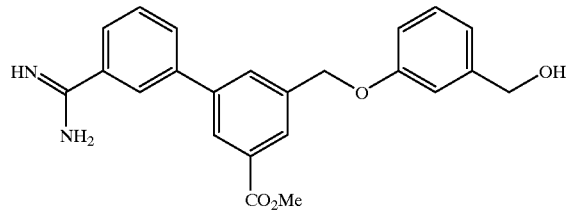

The compound obtained in the production example 21 was used and reacted by a method similar to the method in the example 11 to obtain 39 mg of the title compound. Yield: 33%.

MS (M+1)=391

[Production Example 22]

3-(3-cyanophenyl)-5-((4-(methylamino)phenoxy)methyl)benzoic acid methyl ester

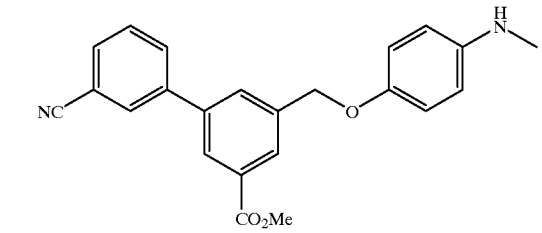

4-methylaminophenol was used instead of the 2-amino-3-hydroxypyridine and reacted by a method similar to the method in the production example 12 to obtain 75 mg (yield: 54%) of the title compound.

$^1$H NMR (270 MHz): δ (CDCl$_3$) 8.2–6.6(m, 11H), 5.12(s, 2H), 3.96(s, 3H), 2.92(s, 3H)

[Example 16]

3-(3-amidinophenyl)-5-((4-(methylamino)phenoxy)methyl)benzoic acid methyl ester

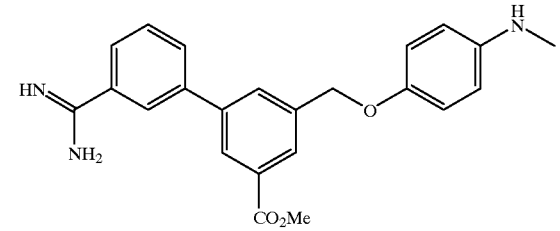

The compound obtained in the production example 22 was used and reacted by a method similar to the method in the example 11 to obtain 15 mg (10%) of the title compound. Colorless solid.

$^1$H NMR (270 MHz): δ (DMSO-d6) 8.3–6.6(m, 11H), 5.12(s, 2H), 3.88(s, 3H), 2.91(s, 3H)

[Production Example 23]
3-(3-cyanophenyl)-5-((4-(N,N-dimethylamino)phenoxy)methyl)benzoic acid methyl ester

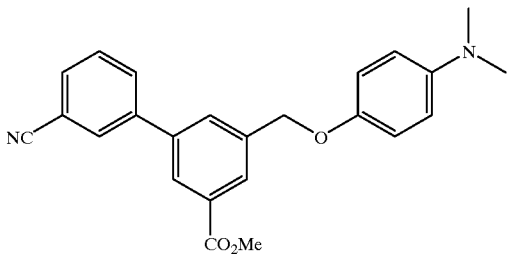

30 mg of the compound obtained in the production example 22 was dissolved in 3 ml of DMF, mixed with 17 mg of methyl iodide and 17 mg of potassium carbonate, stirred overnight and then poured into a mixture liquid of water with ethyl acetate to extract with the ethyl acetate. The obtained ethyl acetate solution was dried, concentrated and purified by silica gel column chromatography to obtain 18 mg (57%) of the title compound.
$^1$H NMR (270 MHz): δ (CDCl$_3$) 8.2–6.5(m, 11H), 5.10(s, 2H), 3.96(s, 3H), 2.91(s, 6H)

[Example 17]
3-(3-amidinophenyl)-5-((4-(N,N-dimethylamino)phenoxy)methyl)benzoic acid methyl ester

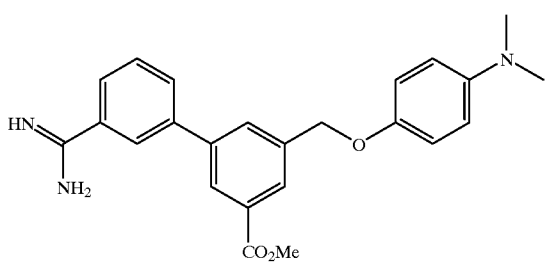

The compound obtained by the production example 23 was used and reacted by a method similar to the method in the example 11 to obtain 5 mg (15%) of the title compound.
$^1$H NMR (270 MHz): δ (DMSO-d6) 8.3–6.5(m, 11H), 5.11(s, 2H), 3.93(s, 31), 2.92(s, 6H)

[Production Example 24]
5-hydroxy-2-tert-butyloxycarbonyl-isoindoline

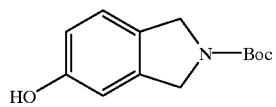

500 mg of 5-hydroxyisoindoline hydrobromide obtained according to a method shown in Japanese Unexamined Publication (Kokai) Number 2-62875 was dissolved in a mixture solvent comprising 8 ml of water and 15 ml of 1,4-dioxane, mixed with 580 mg of di-tert-butyl carbonate and 2.3 ml of a 1N aqueous solution of sodium hydroxide, stirred at room temperature for 2 hours, and then poured into an aqueous solution of ammonium chloride. The mixture was extracted with ethyl acetate, and the obtained organic layer was separated and then dried over magnesium sulfate. The solvent was distilled away to obtain 481 mg (88%) of the title compound as the crude product.

$^1$H NMR (270 MHz): δ (CDCl$_3$) 7.3–6.7(m, 3H), 4.39(d, J=12 Hz, 41), 1.51(s, 9H)

[Production Example 25]
3-(3-cyanophenyl)-5-(2-((tert-butyl)oxycarbonyl)isoindolin-5-yloxymethyl)benzoic acid methyl ester

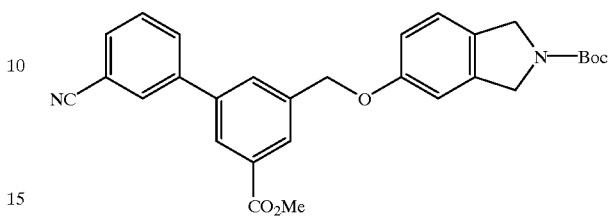

5-hyroxyisoindoline-2-carboxylic acid tert-butyl ester was used instead of 2-amino-3-hydroxypyridine and reacted by a method similar to the method in the production example 12 to obtain 184 mg (quant.) of the title compound.
$^1$H NMR (270 MHz): δ (CDCl$_3$) 8.2–6.8(m, 10H), 5.17(s, 2H), 4.7–4.5(m, 4H), 3.97(s, 3H), 1.51(s, 9H)

[Example 18]
3-(3-amidinophenyl)-5-(isoindoln-5-yloxymethyl)benzoic acid methyl ester

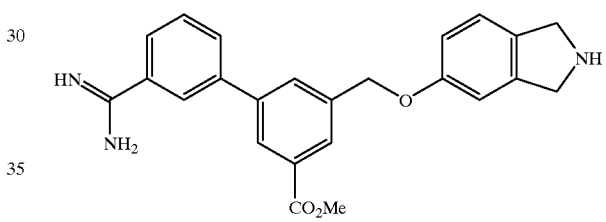

The compound obtained in the production example 22 was used and reacted by a method similar to the method in the example 11 to obtain 70 mg (41%) of the title compound.
$^1$H NMR (270 MHz): δ (DMSO-d6) 8.4–6.8(m, 10H), 5.27(s, 2H), 4.15(d, J=11Hz, 4H), 3.92(s, 3H)

[Example 19]
3-(3-amidinophenyl)-5-((2-(iminoethyl)isoindolin-5-yloxymethyl)benzoic acid methyl ester

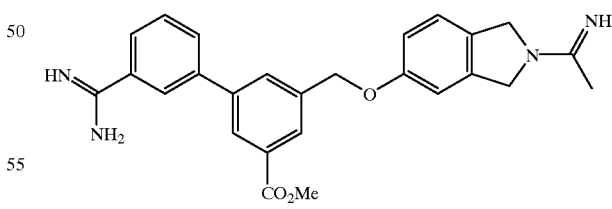

40 mg of the compound obtained in the example 18 was dissolved in 5 ml of ethanol, mixed with 60 mg of ethylacetimidate hydrochloride and 0.10 ml of triethylamine and then stirred overnight. The solvent was distilled away, and the residue was purified by reversed phase HPLC to obtain 30 mg (70%) of the title compound. Colorless solid.
$^1$H NMR (270 MHz): δ (DMSO-d6) 8.4–7.0(m, 10H), 5.31(s, 2H), 4.83(dd, J 11 Hz, 60 Hz, 4H), 3.92(s, 3H), 2.34(s, 3H), 1.78(s, 3H)

[Production Example 26]

3-(3-cyanophenyl)-6-(hydroxymethyl)benzoic acid methyl ester

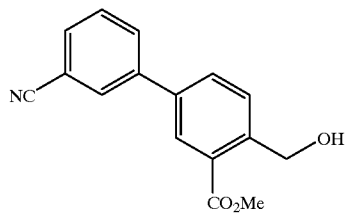

6-hydroxymethyl-3-bromobenzoic acid methyl ester was used instead of the 5-hydroxymethyl-3-iodobenzoic acid methyl ester and reacted similarly as in the production example 4 to obtain 305 mg (73%) of the title compound.

$^1$H NMR (270 MHz): δ (CDCl$_3$) 8.1–7.4(m, 7H), 4.78(d, J=5.9 Hz, 2H), 3.95(s, 3H), 1.72(t, J=5.9 Hz, 1H)

[Production Example 27]

3-(3-cyanophenyl)-6-((3-(N-Boc-aminomethyl)phenoxy)methyl)benzoic acid methyl ester

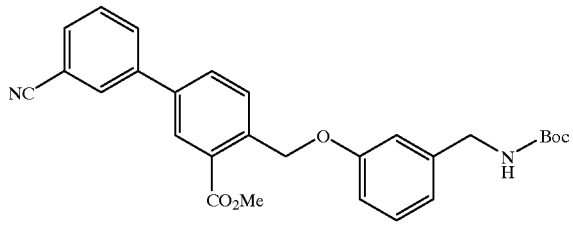

3-(N-Boc-aminomethyl)phenol was used instead of the phenol and reacted with the benzyl alcohol obtained in the production example 26 by a method similar to the method in the production example 5 to obtain 108 mg (45%) of the title compound.

$^1$HNMR(270MHz): δ (CDCl$_3$) 8.1–6.8(m, 11H), 5.12(s, 2H), 4.30(d, J=5.7 Hz, 2H), 3.97(s, 3H), 1.47(s, 9H)

[Example 20]

3-(3-amidinophenyl)-6-((3-aminomethyl)phenoxy)methyl)benzoic acid methyl ester

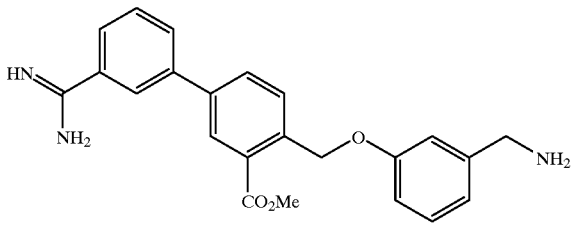

The compound obtained in the production example 27 was used and reacted by a method similar to the method in the example 1 to obtain 16 mg (10%) of the title compound. Colorless solid.

$^1$H NMR (270 MHz): δ (DMSO-d6) 8.2–7.0(m, 1H), 5.19(s, 2H), 4.0 (m, 21), 3.93(s, 3H)

[Production Example 28]

3-(4-(hydroxymethyl)phenyl)benzonitrile

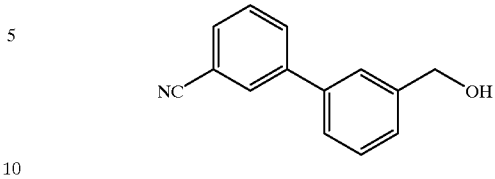

3-iodobenzyl alcohol was used instead of the 5-hydroxymethyl-3-iodobenzoic acid methyl ester and reacted by a method similar to the method in the production example 4 to obtain 5.5 g (75%) of the title compound $^1$H NMR (270 MHz): δ (CDCl$_3$) 8.0–7.3(m, 8H), 4.79(d, J=5,6 Hz, 2H), 1.78(d, J=5.6 Hz, 1H)

[Production Example 29]

1-hydroxybicyclo[3.3.1]nonan-3-one

50.58 g of cyclohexenone and 72.95 g of methyl acetoacetate were measured and placed in a 1,000 ml flask. 300 ml of methanol was added to prepare the homogeneous solution. The solution was gradually mixed with 101.53 g of 28% sodium methoxide, and the mixture was refluxed in the flask equipped with a Dimroth condenser for 72 hours. The reaction solution was cooled, mixed with 100 ml of an aqueous solution containing 72.12 g of potassium hydroxide, and further refluxed for 13 hours. After the reaction was finished, the solvent was distilled away from the reaction solution under reduced pressure, and the residue was extracted with dichloromethane. The obtained organic layers were integrated, washed with a saturated aqueous solution of sodium chloride, and then dried over MgSO$_4$. The solvent was distilled away under reduced pressure, and the residue was again dissolved in diethyl ether. The solution was reversibly extracted with water, and the obtained water layers were integrated and concentrated. The residue was recrystallized from diethyl ether to obtain the title compound as white crystals (41.19g, 50%).

$^1$H NMR (270 MHz): δ (CDCl$_3$) 2.8–2.2(m, 6H), 2.2–1.2 (m, 8H)

[Production Example 30]

2,2,2-trichloro-1-(phenylmethoxy)ethanimine

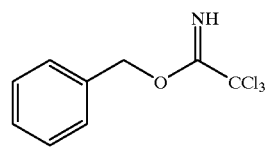

0.868 g of 60% sodium hydroxide was measured and placed in a 100 ml flask with a two-way cock, and the gas in the flask was replaced with nitrogen. The sodium hydroxide was twice washed with hexane, and then dried under reduced pressure. The gas in the flask was again replaced with nitrogen, and 20 ml of diethyl ether was then added to form a suspension. The flask was immersed in an ice water bath, and the suspension was stirred for about five minutes.

20 ml of an ether solution containing 7.19 g of benzyl alcohol was added by the use of a cannula, and the reaction solution was stirred at such a temperature for 20 minutes, mixed with 10 ml of trichloroacetonitrile dropwisely added thereto, and stirred for 2 hours, while the temperature of the solution was gradually raised up to room temperature. After the reaction was finished, the reaction solution was mixed with a methanol/hexane solution, and further stirred for 3 hours. The insolubles were filtered off. The filtrate was concentrated under reduced pressure, and then again mixed with hexane. The impurities were filtered off. The solvent was distilled away from the filtrate under reduced pressure to obtain the title compound as a yellow oil (14.84 g, 88%).

$^1$H NMR (270 MHz): δ (CDCl$_3$) 8.5–8.3(m, 1H), 7.5–7.3 (m, 5H), 5.35(s, 2H)

[Production Example 31]
1-(phenylmethoxy)bicyclo[3.3.1]nonan-3-one

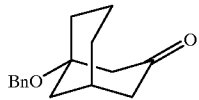

A diethyl ether solution of 260 mg of 2,2,2-trichloro-1-(phenylmethoxy)ethanimine synthesized in the production example 30 was added to 4 ml of a diethyl ether solution of the compound obtained in the production example 29 to prepare the homogeneous solution, and the flask was immersed in an ice water bath. The solution in the flask was mixed with 10 μl of trifluoromethanesulfonic acid, gradually heated up to room temperature, and simultaneously stirred for 17 hours. After the reaction was finished, the reaction solution was diluted with ethyl acetate and extracted. The obtained organic layers were integrated, sequentially washed with a saturated aqueous solution of sodium bicarbonate and with a saturated aqueous solution of sodium chloride, and then dried over Na2SO$_4$. The solvent was distilled away under reduced pressure, and the residue was purified by column chromatography to obtain the title compound (120 mg, 70%).

$^1$H NMR (270 MHz): δ (CDCl$_3$) 7.5–7.2(m, 5H), 4.51(d, J=1.0 Hz), 2.8–2.3(m, 5H), 2.1–1.9(m, 3H), 1.8–1.2(m, 5H)

[Production Example 32]
1-(phenylmethoxy)-3-prop-2-enylbicyclo[3.3.1]nonan-1-ol

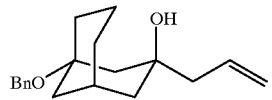

6.11 g of anhydrous cerium chloride was placed in a 200 ml flask with a two-way cock, heated with a heat gun, and simultaneously dried. The gas in the flask was replaced with nitrogen. 60 ml of THF was added to prepare the suspension, which was stirred at room temperature for two hours. The suspension was mixed with 20 ml of a THF solution containing 2 g of 1-(phenylmethoxy)bicyclo[3.3.1]nonan-3-one under the flow of nitrogen, and then stirred at room temperature for one hour. The flask was immersed in an ice water bath to cool the mixture, to which 16 ml of a 1M allyl magnesium bromide solution was gradually dropwisely added. The reaction solution was stirred at such a temperature for one hour, and then treated with an aqueous solution of ammonium chloride cooled with ice. The treated solution was extracted with diethyl ether, and the obtained organic layers were integrated, sequentially washed with a saturated aqueous solution of sodium bicarbonate and with an aqueous solution of sodium chloride, and then dried over Na2SO$_4$. The solvent was distilled away under reduced pressure, and the residue was purified by silica gel column chromatography to obtain the title compound as an oily substance (1.66 g, 71%).

$^1$H NMR (270 MHz): δ (CDCl$_3$) 7.5–7.2(m, 5H), 6.0–5.8 (m, 1H), 5.3–5.1(m, 2H), 4.50(d, J=2.0 Hz, 2H), 2.9–2.7(m, 1H), 2.27(br, 1H), 2.25(d, J=7.3 Hz, 21), 2.0–1.5(m, 12H)

[Production Example 33]
3-(methoxymethoxy)-1-(phenylmethoxy)-3-prop-2-enylbicyclo[3.3.1]nonane

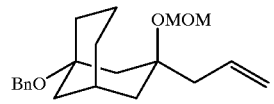

28.2 mg of the compound obtained in the production example 32 was measured, placed in a 25 ml flask, and mixed with 1 ml of diisopropylethylamine to produce a homogeneous solution. The solution was stirred at room temperature for 8 hours. The reaction solution was diluted with diethyl ether and then extracted. The obtained organic layers were integrated, washed with a saturated aqueous solution of sodium chloride, and then dried over Na2SO$_4$. The solvent was distilled away. The residue was purified by silica gel column chromatography to obtain the title compound as an oil (31.3 mg, 94%).

$^1$H NMR (270 MHz): d(CDCl$_3$) 7.5–7.2(m, 5H), 6.0–5.7 (m, 1H), 5.0–5.2(m, 2H), 4.75(s, 2H), 4.50(s, 2H), 3.41(s, 3H), 1.4–2.5(m, 14H)

[Production Example 34]
(3-(3-(methoxymethoxy)-1-(phenylmethoxy)bicyclo[3.3.1]non-3-yl)propan-1-ol

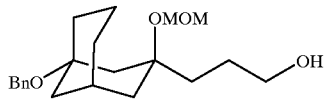

411 mg of 3-(methoxymethoxy)-1-(phenylmethoxy)-3-prop-2-enylbicyclo[3.3.1]nonane was measured, placed in a 50 ml flask, and dried under reduced pressure. The gas in the flask was replaced with nitrogen, and THF was added under the flow of nitrogen to produce the homogeneous solution. While the flask was immersed in an ice water bath to cool the solution, 0.62 ml of a 1M borane·THF solution was gradually and dropwisely added to the cooled solution. The reaction solution was stirred at such a temperature for 1.5 hour. After it was confirmed by TLC that the raw materials were eliminated, 0.5 ml of methanol, 1 ml of an 1M aqueous solution of sodium hydroxide and 4 ml of a 30% aqueous solution of hydrogen peroxide were sequentially added to the reaction solution, and further stirred for 40 minutes. The reaction solution was diluted with diethyl ether, sequentially washed with an aqueous solution of sodium thiosulfate, an aqueous solution of sodium bicarbonate, and a saturated aqueous solution of sodium chloride and then dried. The solvents were distilled away under reduced pressure, and the residue was purified by silica gel column chromatography to obtain the title compound as an oily substance (348 mg, 80%).

¹H NMR (270 MHz): d (CDCl₃) 7.5–7.2(m, 5H), 4.70(s, 2H), 4.49(s, 2H), 3.7–3.6(br, 2H), 3.41(s, 3H), 2.5–1.3(m, 17H)

[Production Example 35]

3-(3-(methoxymethoxy)-1-(phenylmethoxy)bicyclo[3.3.1]non-3-yl)propyl p-toluenesulfonate

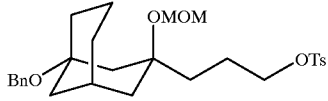

47 mg of the compound obtained in the production example 34 was measured, placed in a 25 ml flask, and mixed with dichloromethane to produce the homogeneous solution. The solution was sequentially mixed with 25 μl of pyridine and with 31.4 mg of p-toluenesulfonic chloride, and stirred at room temperature for 3 hours. The solution was mixed with 20 μl of triethylamine, and further stirred for 22 hours. The reaction solution was diluted with diethyl ether and extracted. The obtained organic layers were integrated, washed with a saturated aqueous solution of sodium chloride and then dried. The solvent was distilled away under reduced pressure, and the residue was purified by silica gel column chromatography to obtain the title compound (39.0 mg, 58%).

¹H NMR (270 MHz): δ (CDCl₃) 7.9–7.2(m, 9H), 4.61(s, 2H), 4.47(s, 2H), 4.01(t, J=6.3 Hz, 2H), 3.34(s, 3H), 2.44(s, 3H), 1.4–2.4(m, 17H)

[Production Example 36]

(3-(3-azidopropyl)-3-(methoxymethoxy)-1-(phenylmethoxy) bicyclo[3.3.1]none

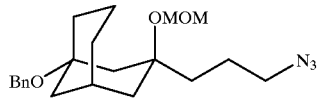

182.0 mg of the compound obtained by the method in the production example 35 and 53.7 mg of sodium azide were measured and placed in a 25 ml flask, mixed with 4 ml of dimethylformamide and then stirred at room temperature for 21 hours. After it was confirmed by TLC that the raw materials were eliminated, the reaction solution was diluted with diethyl ether and extracted. The obtained organic layers were integrated, washed with a saturated aqueous solution of sodium chloride, and then dried. The solvent was distilled away under reduced pressure, and the residue was purified by silica gel column chromatography to obtain the title compound (122.6 mg, 91%).

¹H NMR (270 MHz): d (CDCl₃) 7.5–7.1(m, 5H), 4.69(s, 2H), 4.50(s, 2H), 3.41(s, 3H), 3.26(t, J=6.3 Hz, 2H), 2.5–1.5 (m, 17H).

[Production Example 37]

(3-(3-(methoxymethoxy)-1-(phenylmethoxy) bicyclo[3.3.1]non-3-yl) propylamine

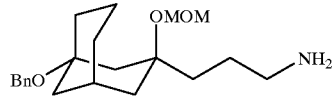

0.99 g of the compound obtained by the method in the production example 36 and 97 mg of Pd·CaCO₃ were measured, placed in a 50 ml side arm reactor, and then dried. The gas in the reactor was replaced with nitrogen, and 10 ml of ethanol was added to produce the suspension. The gas in the flask was replaced with hydrogen, and then the suspension was stirred for 2 hours at room temperature. After it was confirmed by TLC that the raw materials were eliminated, the reaction solution was filtered. The solvent was distilled away from the filtrate under reduced pressure. The residue was diluted with diethyl ether and then extracted with diluted hydrochloric acid. The obtained aqueous layers were integrated, mixed with sodium bicarbonate to produce the weakly alkaline aqueous solution, which was again extracted with diethyl ether. The obtained organic layers were integrated, washed with a saturated aqueous solution of sodium chloride and then dried. The solvent was distilled away under reduced pressure to obtain the title compound (0.820 g, 89%).

¹H NMR (270 MHz): δ (CDCl₃) 7.4–7.1(m, 5H), 4.69(s, 2H), 4.50(s, 2H), 3.41(s, 3H), 1.3–2.8(m, 19H)

[Production Example 38]

2,2,2-trifluoro-N-(3-(3-(methoxymethoxy)-1-(phenylmethoxy) bicyclo[3.3.1]non-3-yl)propyl) ethanamide

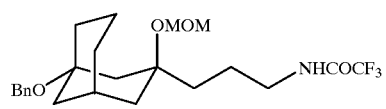

20 ml of a dichloromethane solution containing 0.82 g of the compound obtained in the production example 37 was sequentially mixed with 1.0 ml of pyridine and 1.0 ml of trifluoroacetic anhydride, and then stirred at room temperature for one hour. After the finish of the reaction was confirmed by TLC, the solvent was distilled away from the reaction solution under reduced pressure. The residue was diluted with diethyl ether, and then extracted. The obtained organic layers were integrated, washed with a saturated aqueous solution of sodium chloride and then dried. The solvent was distilled away under reduced pressure to obtain the title compound (0.998 g, 95%).

¹H NMR (270 MHz): d (CDCl₃) 7.5–7.1(m, 6H), 4.71(d, J=1.3 Hz, 2H), 4.50(s, 2H), 3.43(s, 3H), 3.31(ABqJ=6.3, 5.3 Hz, 2H), 2.5–1.4(m, 17H)

[Production Example 39]
2,2,2-trifluoro-N-(3-(1-hydroxy-3-(methoxymethoxy)bicyclo[3.3.1]non-3-yl)propyl)ethanamide

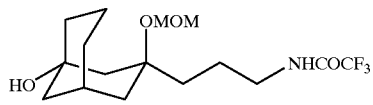

998 mg of the compound obtained in the production example 38 and 435 mg of 10% palladium-carbon were measured and placed in a 50 ml side arm flask. The gas in the flask was replaced with nitrogen, and 10 ml of ethanol was added to produce the suspension. The gas in the flask was replaced with hydrogen, and the suspension was stirred at room temperature for 6 days. After the reaction was finished, the reaction asolution was filtered, and the filtrate was concentrated to obtain the title compound as an oily substance (684 mg, 86%).

$^1$H NMR (270 MHz): δ (CDCl$_3$) 7.4–7.3(br, 1H), 4.71(d, J=1.3 Hz, 2H), 3.49(s, 3H), 3.32(Abq, J=6.3, 5.3 Hz, 2H), 1.4–2.5(m, 17H)

[Production Example 40]
3-(3-((2,2,2-trichloro-1-iminoethoxy)methyl)phenyl) benzonitrile.

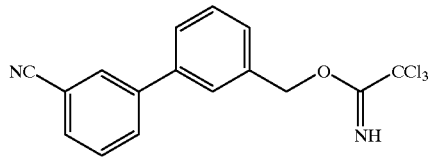

3-(3-cyanophenyl)benzyl alcohol was used instead of the benzyl alcohol and reacted by a method similar to the method in the production example 28 to obtain the title compound (285 mg, 88%).

$^1$H NMR (270 MHz): δ (CDCl$_3$) 8.6–8.3(br, 1H), 8.0–7.4 (m, 8H), 5.42(s, 2H)

[Production Example 41]
N-(3-(1-(((3-(3-cyanophenyl)phenyl)methoxy)methyl) bicyclo[3.3.1]non-3-ylidene)propyl)-2,2,2-trifluoroethanamide

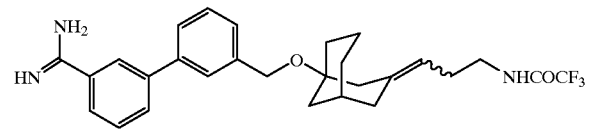

245 mg of the alcohol obtained in the production example 39 was placed in a 25 ml flask, and the gas in the flask was replaced with nitrogen. The alcohol was mixed with 2 ml of diethyl ether, cooled at 0° C., stirred and simultaneously mixed with 4 ml of a diethyl ether solution containing 377 mg of the trichloroimldate obtained in the production example 40. While cooled with ice and stirred, the mixture was mixed with 10 μl of trifluoromethanesulfonic acid, stirred at 0° C. for 18 hours, further mixed with 10 μl of trifluoromethanesulfonic acid, stirred at 0° C. for 4 hours, and then mixed with a saturated aqueous solution of sodium bisulfite to stop the reaction. The reaction solution was extracted with ethyl acetate, and the obtained organic layer was washed with water and then with a saturated aqueous solution of sodium chloride, and dried over magnesium sulfate. The solvent was distilled away under reduced pressure, and the residue was purified by silica gel chromatography to obtain 242 mg of the title compound (a mixture of E and Z).

$^1$H NMR (270 MHz): δ (CDCl$_3$) 7.9–7.8(m, 2H), 7.6–7.4 (m, 6H), 6.6(bs, 1H), 5.4(s, 2H), 4.6(m, 4H), 3.4(m, 4H), 2.7–1.4(m, 71)

[Example 2 1]
3-(3-((3-(2,2,2-trifluoroacetylamino)propylidene)bicyclo[3.3.1]nonyloxy) methyl)phenyl)benzamidine

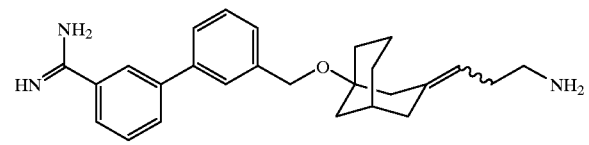

42 mg of ammonium chloride was placed in a 50 ml flask, and the gas in the system was replaced with nitrogen. 5 ml of anhydrous toluene was added into the flask, and cooled at 0° C. While stirred, the mixture was mixed with 0.77 ml of triethylaluminum (a 1.0M hexane solution) and stirred at room temperature for 2 hours. After once cooled at 0° C., the reaction mixture solution was mixed with 10 ml of a toluene solution containing 124 mg of the compound obtained in the production example 42, and then stirred at 80° C. for 16 hours. After the elimination of the raw materials was confirmed, the reaction solution was mixed with a suspension of 2.0 g of silica gel (10 ml of chloroform) to stop the reaction. The obtained insolubles were filtered out and, washed with diethyl ether, suspended in ethanol and further filtered. The filtrate was concentrated and dried under reduced pressure, and then suspended in ethyl acetate. The insolubles were filtered off, and the solvent was distilled away under reduced pressure to obtain 39 mg of the crude product. The crude product was fractionated and purified by HPLC to obtain 29 mg of the compound. Yield: 22%.

$^1$H NMR (270 MHz): δ (CD$_3$OD) 7.9–7.8(m, 2H), 7.6–7.4(m, 6H), 6.6(bs, 1H), 5.5(s, 2H), 4.6(m, 4H), 3.3(m, 4H), 2.7–1.5(m, 7H)

[Example 22]
3-(3-((3-(3-aminopropylidene)bicyclo[3.3.1]nonyloxy) methyl)phenyl) benzamidine 9.9 mg of the compound obtained in the example 22 was placed in a 50 ml flask, and then mixed with 1.5 ml of methanol and 1.5 ml of water. While stirred at room temperature, the mixture was mixed with 198 ml of a 1N aqueous solution of sodium hydroxide, and further stirred at room temperature for 16 hours. After the progress of the reaction was confirmed by HPLC, the reaction solution was mixed with 200 ml of a 1N aqueous solution of sulfuric acid to stop the reaction. The reaction solvent was distilled away under reduced pressure to obtain 12 mg of the crude product. The obtained product was fractionated and purified by HPLC to obtain 4.6 mg of the title compound. Yield: 58%.

$^1$H NMR (270 MHz): δ (CD$_3$OD) 7.9–7.8(m, 2H), 7.6–7.4(m, 6H), 6.6(bs, 1H), 5.6(s, 2H), 4.7(m, 4H), 3.4(m, 4H), 2.7–1.5(m, 7H)

[Production Example 42]

5-(3-cyanophenyl)-3-((2,2,2-trichloro-1-iminoethoxy)methyl)benzoic acid methyl ester

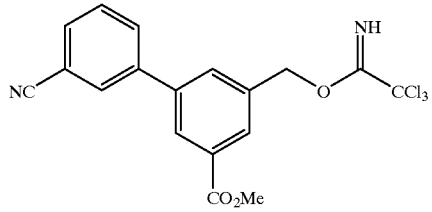

The compound obtained in the production example 4 was used and reacted by a method similar to the method in the production example 28 to obtain 1.5 g (85%) of the title compound.

MS (M+1)=411

[Production Example 43]

5-(3-cyanophenyl)-3-((phenylmethoxy)methyl)benzoic acid methyl ester

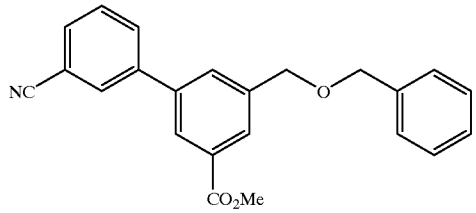

The compound obtained in the production example 42 was used and reacted with benzyl alcohol by a method similar to the method in the production example 29 to obtain 56 mg (12%) of the tittle compound.

MS (M+1)=358

[Example 23]

5-(3-amidinophenyl)-3-((phenylmethoxy)methyl)benzoic acid methyl ester

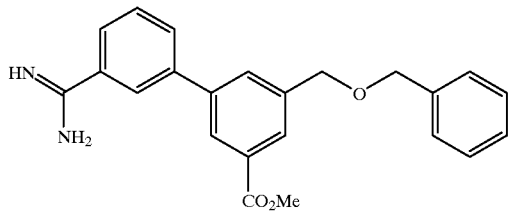

The compound obtained in the production example 43 was used and reacted by a method similar to the method in the example 11 to obtain 12 mg (65%) of the title compound.

MS (M+1)=375

[Production Example 44]

5-(3-cyanophenyl)-3-(((4-(methylethyl)phenyl)methoxy)methyl)benzoic acid methyl ester

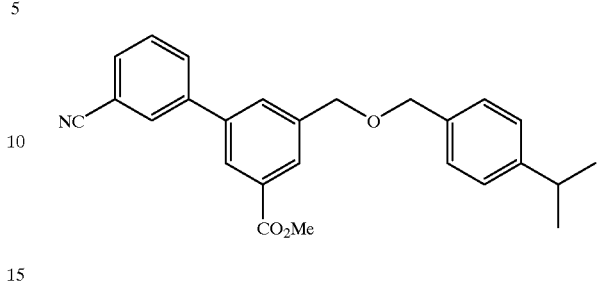

The compound obtained in the production example 42 was reacted with 4-(methylethyl)phenylmethanol by a method similar to the method in the production example 29 to obtain 50 mg (10%) of the title compound.

MS (M+1)=400

[Example 24]

5-(3-amidinophenyl)-3-(((4-(methylethyl)phenyl)methoxy)methyl)benzoic acid methyl ester

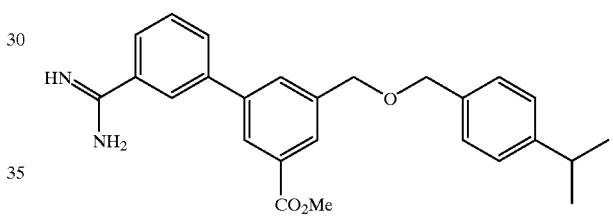

The compound obtained in the production example 44 was reacted by a method similar to the method in the example 11 to obtain 14 mg (40%) of the title compound.

MS (M+1)=417

[Production Example 45]

3-(((3-(((tert-butoxy)carbonylamino)methyl)phenyl)methoxy)methyl)-5-(3-cyanophenyl)benzoic acid methyl ester

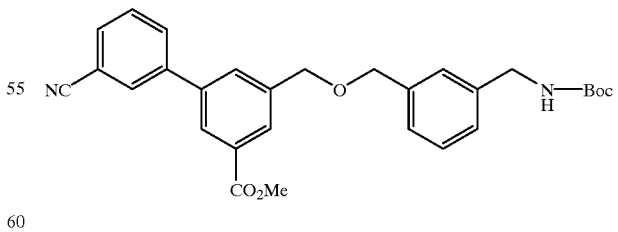

The compound obtained in the production example 42 was reacted with (tert-butoxy)-N-((3-(hydroxymethyl)phenyl)methyl)formamide similarly as in the production example 29 to obtain 32 mg (11%) of the title compound.

MS (M+1)=487

[Example 25]
5-(3-amidinophenyl)-3-(((3-(aminomethyl)phenyl)methoxy)methyl)benzoic acid methyl ester

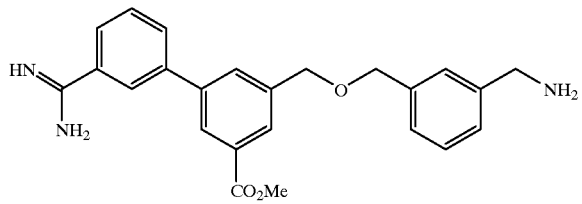

The compound obtained in the production example 45 was reacted by a method similar to the method in the example 11 to obtain 21 mg (55%) of the title compound.
MS (M+1)=404

[Experimental Example 1]
Measurement of activated blood coagulation factor X (FXa)-inhibiting action A specimen was dissolved in water or in water containing an organic solvent (DSMO, ethanol or methanol) in a proper concentration to prepare a specimen. 70 μl of the specimen stepwisely diluted with water was mixed with 90 μl of a 100 mM Tris buffer solution (pH 8.4), 20 μl of a 50 mM Tris buffer solution (pH 8.4) of 50 mU/ml human FXa, and a 2 mM substrate (Daiichikagaku. S-2765), incubated for 30 minutes, mixed with 50 μl of 50% acetic acid, and then subjected to the measurement of absorbance (A405). A blank was prepared by adding the Tris buffer solution instead of the FXa, and a control was prepared by adding water instead of the specimen. A 50% inhibition activity ($IC_{50}$) was determined, and used as the index of the FXa-inhibiting action.

Consequently, inhibition activities ($IC_{50}$) of 0.1 to 1 μM, 1 were recognized on the compounds of the examples 18 and 19, respectively. Inhibition activities ($IC_{50}$) of 1 to 10 μM were recognized on the compounds of the examples 3, 4, 5, 6, 9, 10, 12, 15 and 23, respectively. Inhibition activities ($IC_{50}$) of 10 to 100 μM were recognized on the compounds of the examples 11, 15 and 20, respectively.

[Experimental Example 2]
Measurement of thrombin inhibition action

70 μl of the specimen stepwisely diluted with water was mixed with 90 μl of a 100 mM Tris buffer solution (pH 8.4), 20 μl of a 50 mM Tris buffer solution (pH 8.4) of 1U/ml human thrombin, and a 2 mM substrate (Daiichikagaku. S-2238), incubated for 30 minutes, mixed with 50 μl of 50% acetic acid, and then subjected to the measurement of absorbance (A405). A blank was prepared by adding the Tris buffer solution instead of the thrombin, and a control was prepared by adding water instead of the specimen. A 50% inhibition activity ($IC_{50}$) was determined, and used as the index of the thrombin inhibition action.

Consequently, inhibition activities ($IC_{50}$) of 10 to 100 μM were recognized on the compounds of the examples 16, 19, respectively, but the compounds of the examples 5, 6, 9, 10, 11, 12, 13 and 20 were recognized to have the weak inhibition activities ($IC_{50}$) of >100 μM, respectively. It was therefore clarified that the biphenylamidine compound of the present invention was the Xa-selective inhibitor.

Measurement of anticoagulant action (APTT)

100 μl of the specimen was added to 100 μl of a normal human plasma (Ci-Trol®) produced by DADE., incubated at 37° C. for one minute, mixed with 100 μl of APTT reagent (produced by DADE) kept at 37° C., incubated at 37° C. for two minutes, mixed with 100 μl of a 25 mM solution of calcium chloride and then subjected to the measurement of coagulation time by the use of a coagulation measurement device made by AMELUNG. A coagulation time obtained by adding physiological salt solution instead of the specimen was used as a control. A specimen concentration (CT2) for prolonging the coagulation time into a double time was determined, and used as an index for the anticoagulant action.

Consequently, the activities represented by specimen concentrations (CT2) of 1 to 10 μM were recognized on the compounds of the examples 9, 18 and 19, respectively, and the activities represented by specimen concentrations (CT2) of 10 to 100 μM were recognized on the compounds of the examples 5, 6, 10, 11, 12, 13, and 20, respectively.

Utilization in industry

The biphenylamidine derivative of the present invention or a pharmaceutically acceptable salt thereof has the action for inhibiting the FXa activity, and can be used as a preventing agent and/or a treating agent which can clinically be applied to thromboembolic diseases such as cardiac infarction, cerebral thrombosis, peripheral arterial thrombosis, and deep venous thrombosis as FXa inhibitors.

TABLE 1

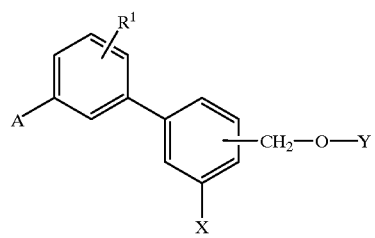

| Compound Number | A | R¹ | X | Substitution Position of —CH2—O—Y | Y |
|---|---|---|---|---|---|
| 1 | H2N—C(=NH)— | —H | —CO2H | meta-position | 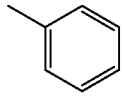 |

TABLE 1-continued
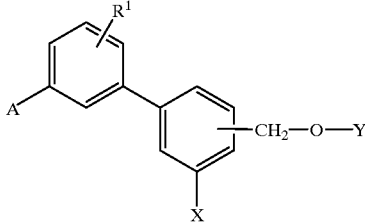
| Compound Number | A | R¹ | X | Substitution Position of —CH2—O—Y | Y |
|---|---|---|---|---|---|
| 2 | H2N—C(=NH)— | —H | —CO2H | meta-position | 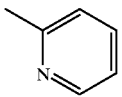 |
| 3 | H2N—C(=NH)— | —H | —CO2H | meta-position | 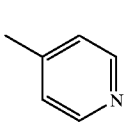 |
| 4 | H2N—C(=NH)— | —H | —CO2H | meta-position | 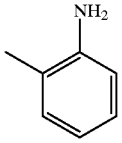 |
| 5 | H2N—C(=NH)— | —H | —CO2H | meta-position | 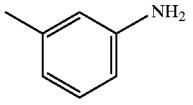 |
| 6 | H2N—C(=NH)— | —H | —CO2H | meta-position | 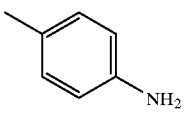 |
| 7 | H2N—C(=NH)— | —H | —CO2H | meta-position | 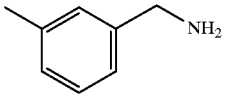 |
| 8 | H2N—C(=NH)— | —H | —CO2H | meta-position | 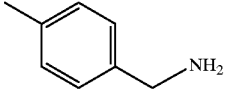 |
| 9 | H2N—C(=NH)— | —H | —CO2H | meta-position | 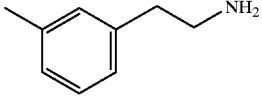 |
| 10 | H2N—C(=NH)— | —H | —CO2H | meta-position | 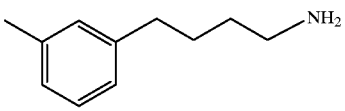 |
| 11 | H2N—C(=NH)— | —H | —CO2H | meta-position | |

TABLE 1-continued
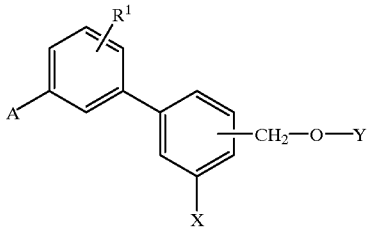
| Compound Number | A | R¹ | X | Substitution Position of —CH2—O—Y | Y |
|---|---|---|---|---|---|
| 12 | H2N—C(=NH)— | —H | —CO2H | meta-position | 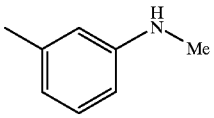 |
| 13 | H2N—C(=NH)— | —H | —CO2H | meta-position | 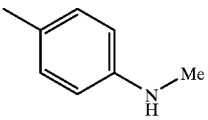 |
| 14 | H2N—C(=NH)— | —H | —CO2H | meta-position | 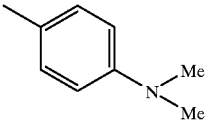 |
| 15 | H2N—C(=NH)— | —H | —CO2H | meta-position | 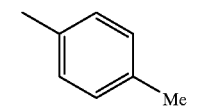 |
| 16 | H2N—C(=NH)— | —H | —CO2H | meta-position | 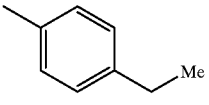 |
| 17 | H2N—C(=NH)— | —H | —CO2H | meta-position | 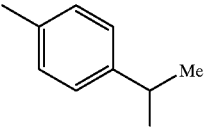 |
| 18 | H2N—C(=NH)— | —H | —CO2H | meta-position | 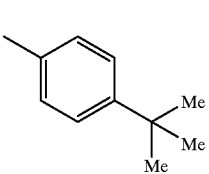 |
| 19 | H2N—C(=NH)— | —H | —CO2H | meta-position | |

TABLE 1-continued
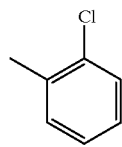
| Compound Number | A | R¹ | X | Substitution Position of —CH2—O—Y | Y |
|---|---|---|---|---|---|
| 20 | H2N—C(=NH)— | —H | —CO2H | meta-position | 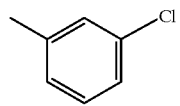 |
| 21 | H2N—C(=NH)— | —H | —CO2H | meta-position | 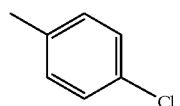 |
| 22 | H2N—C(=NH)— | —H | —CO2H | meta-position | 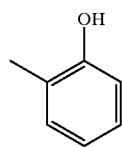 |
| 23 | H2N—C(=NH)— | —H | —CO2H | meta-position | 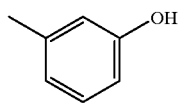 |
| 24 | H2N—C(=NH)— | —H | —CO2H | meta-position | 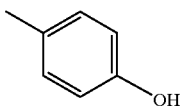 |
| 25 | H2N—C(=NH)— | —H | —CO2H | meta-position | 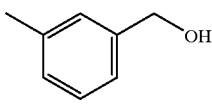 |
| 26 | H2N—C(=NH)— | —H | —CO2H | meta-position | 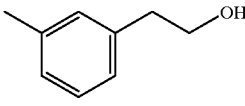 |
| 27 | H2N—C(=NH)— | —H | —CO2H | meta-position | 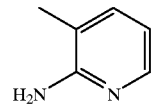 |
| 28 | H2N—C(=NH)— | —H | —CO2H | meta-position | |

TABLE 1-continued
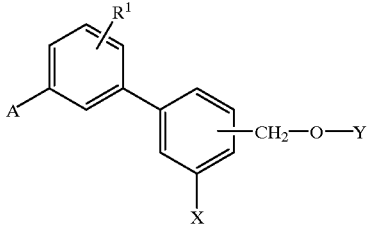
| Compound Number | A | R[1] | X | Substitution Position of —CH2—O—Y | Y |
|---|---|---|---|---|---|
| 29 | H2N—C(=NH)— | —H | —CO2H | meta-position | 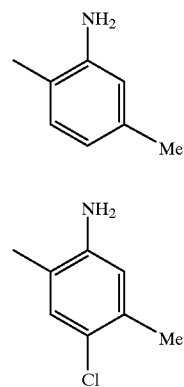 |
| 30 | H2N—C(=NH)— | —H | —CO2H | meta-position | 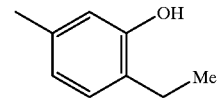 |
| 31 | H2N—C(=NH)— | —H | —CO2H | meta-position | 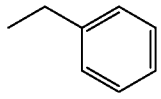 |
| 32 | H2N—C(=NH)— | —H | —CO2H | meta-position | 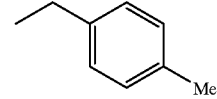 |
| 33 | H2N—C(=NH)— | —H | —CO2H | meta-position | 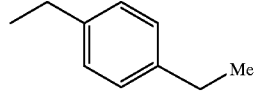 |
| 34 | H2N—C(=NH)— | —H | —CO2H | meta-position | 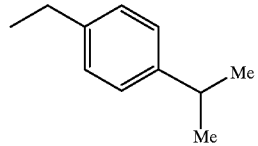 |
| 35 | H2N—C(=NH)— | —H | —CO2H | meta-position | 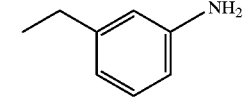 |
| 36 | H2N—C(=NH)— | —H | —CO2H | meta-position |  |

TABLE 1-continued

| Compound Number | A | R¹ | X | Substitution Position of —CH2—O—Y | Y |
|---|---|---|---|---|---|
| 37 | H2N—C(=NH)— | —H | —CO2H | meta-position | 3-ethylbenzylamine |
| 38 | H2N—C(=NH)— | —H | —CO2H | meta-position | 6-methylindoline |
| 39 | H2N—C(=NH)— | —H | —CO2H | meta-position | 1-(1-iminoethyl)-6-methylindoline |
| 40 | H2N—C(=NH)— | —H | —CO2H | meta-position | 5-methylisoindoline |
| 41 | H2N—C(=NH)— | —H | —CO2H | meta-position | 2-(1-iminoethyl)-5-methylisoindoline |
| 42 | H2N—C(=NH)— | —H | —CO2H | meta-position | 5-methylindoline |
| 43 | H2N—C(=NH)— | —H | —CO2H | meta-position | 1-(1-iminoethyl)-5-methylindoline |
| 44 | H2N—C(=NH)— | —H | —CO2H | meta-position | (bicyclo[3.3.1]nonylidene-ethyl)amine |
| 45 | H2N—C(=NH)— | —H | —CO2H | meta-position | N-(bicyclo[3.3.1]nonylidene-ethyl)trifluoroacetamide |

TABLE 1-continued

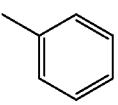

| Compound Number | A | R¹ | X | Substitution Position of —CH2—O—Y | Y |
|---|---|---|---|---|---|
| 46 | H2N—C(=NH)— | —H | —CO2H | ortho-position of X | 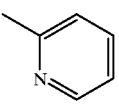 |
| 47 | H2N—C(=NH)— | —H | —CO2H | ortho-position of X | 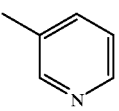 |
| 48 | H2N—C(=NH)— | —H | —CO2H | ortho-position of X | 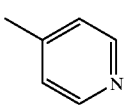 |
| 49 | H2N—C(=NH)— | —H | —CO2H | ortho-position of X | 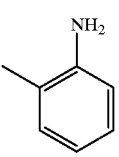 |
| 50 | H2N—C(=NH)— | —H | —CO2H | ortho-position of X | 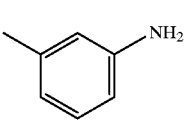 |
| 51 | H2N—C(=NH)— | —H | —CO2H | ortho-position of X | 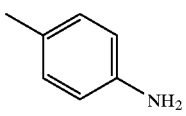 |
| 52 | H2N—C(=NH)— | —H | —CO2H | ortho-position of X | 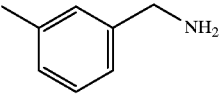 |
| 53 | H2N—C(=NH)— | —H | —CO2H | ortho-position of X | 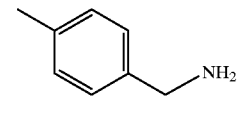 |
| 54 | H2N—C(=NH)— | —H | —CO2H | ortho-position of X | 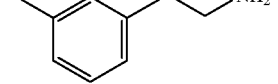 |
| 55 | H2N—C(=NH)— | —H | —CO2H | ortho-position of X | |

TABLE 1-continued
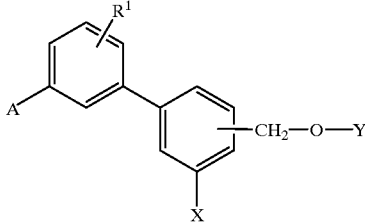
| Compound Number | A | R¹ | X | Substitution Position of —CH2—O—Y | Y |
| --- | --- | --- | --- | --- | --- |
| 56 | H2N—C(=NH)— | —H | —CO2H | ortho-position of X | 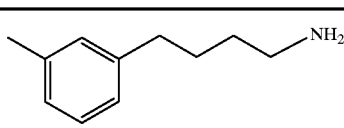 |
| 57 | H2N—C(=NH)— | —H | —CO2H | ortho-position of X | 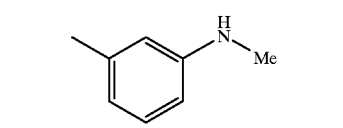 |
| 58 | H2N—C(=NH)— | —H | —CO2H | ortho-position of X | 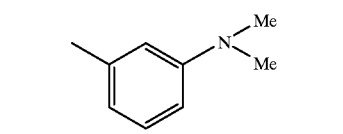 |
| 59 | H2N—C(=NH)— | —H | —CO2H | ortho-position of X | 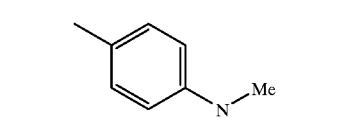 |
| 60 | H2N—C(=NH)— | —H | —CO2H | ortho-position of X | 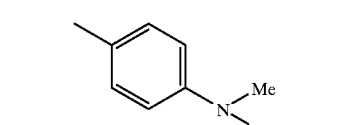 |
| 61 | H2N—C(=NH)— | —H | —CO2H | ortho-position of X | 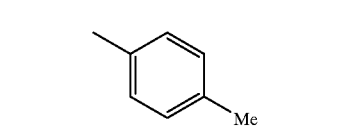 |
| 62 | H2N—C(=NH)— | —H | —CO2H | ortho-position of X | 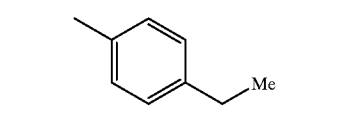 |
| 63 | H2N—C(=NH)— | —H | —CO2H | ortho-position of X | 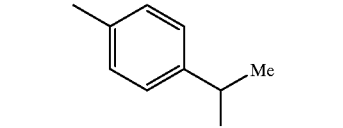 |
| 64 | H2N—C(=NH)— | —H | —CO2H | ortho-position of X | 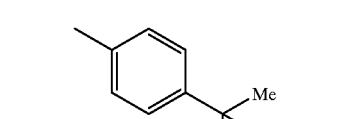 |

TABLE 1-continued
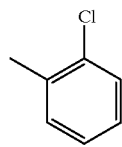
| Compound Number | A | R¹ | X | Substitution Position of —CH2—O—Y | Y |
|---|---|---|---|---|---|
| 65 | H2N—C(=NH)— | —H | —CO2H | ortho-position of X | 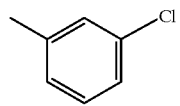 |
| 66 | H2N—C(=NH)— | —H | —CO2H | ortho-position of X | 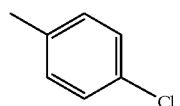 |
| 67 | H2N—C(=NH)— | —H | —CO2H | ortho-position of X | 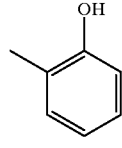 |
| 68 | H2N—C(=NH)— | —H | —CO2H | ortho-position of X | 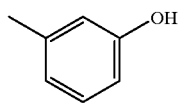 |
| 69 | H2N—C(=NH)— | —H | —CO2H | ortho-position of X | 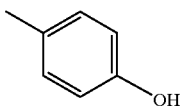 |
| 70 | H2N—C(=NH)— | —H | —CO2H | ortho-position of X | 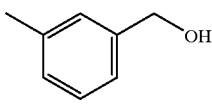 |
| 71 | H2N—C(=NH)— | —H | —CO2H | ortho-position of X | 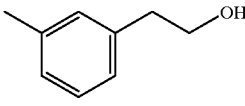 |
| 72 | H2N—C(=NH)— | —H | —CO2H | ortho-position of X | 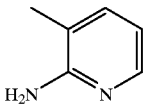 |
| 73 | H2N—C(=NH)— | —H | —CO2H | ortho-position of X |  |

TABLE 1-continued

| Compound Number | A | R¹ | X | Substitution Position of —CH2—O—Y | Y |
|---|---|---|---|---|---|
| 74 | H2N—C(=NH)— | —H | —CO2H | ortho-position of X | 2-amino-5-methylphenyl (NH2, Me) |
| 75 | H2N—C(=NH)— | —H | —CO2H | ortho-position of X | 2-amino-4-chloro-5-methylphenyl (NH2, Me, Cl) |
| 76 | H2N—C(=NH)— | —H | —CO2H | ortho-position of X | 2-hydroxy-... (OH, Me) |
| 77 | H2N—C(=NH)— | —H | —CO2H | ortho-position of X | benzyl |
| 78 | H2N—C(=NH)— | —H | —CO2H | ortho-position of X | 4-methylbenzyl (Me) |
| 79 | H2N—C(=NH)— | —H | —CO2H | ortho-position of X | 1-(4-substituted-phenyl)ethyl (Me) |
| 80 | H2N—C(=NH)— | —H | —CO2H | ortho-position of X | 1-(4-substituted-phenyl)-1-methylethyl (Me, Me) |
| 81 | H2N—C(=NH)— | —H | —CO2H | ortho-position of X | 3-aminobenzyl (NH2) |

TABLE 1-continued
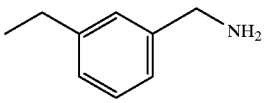
| Compound Number | A | R¹ | X | Substitution Position of —CH2—O—Y | Y |
|---|---|---|---|---|---|
| 82 | H2N—C(=NH)— | —H | —CO2H | ortho-position of X | 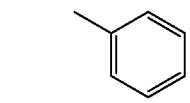 |
| 83 | H2N—C(=NH)— | —H | —CO2Me | meta-position | 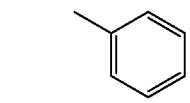 |
| 84 | H2N—C(=NH)— | —H | —CO2Me | meta-position | 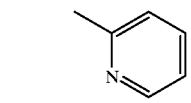 |
| 85 | H2N—C(=NH)— | —H | —CO2Me | meta-position | 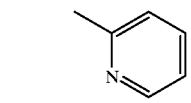 |
| 86 | H2N—C(=NH)— | —H | —CO2Me | meta-position | 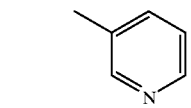 |
| 87 | H2N—C(=NH)— | —H | —CO2Me | meta-position | 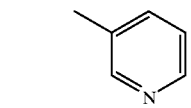 |
| 88 | H2N—C(=NH)— | —H | —CO2Me | meta-position | 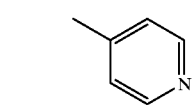 |
| 89 | H2N—C(=NH)— | —H | —CO2Me | meta-position | 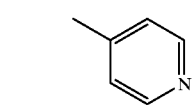 |
| 90 | H2N—C(=NH)— | —H | —CO2Me | meta-position | 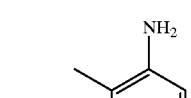 |
| 91 | H2N—C(=NH)— | —H | —CO2Me | meta-position | 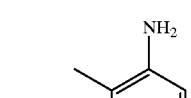 |

TABLE 1-continued

[Structure: biphenyl with R¹, A, X substituents and -CH₂-O-Y group]

| Compound Number | A | R¹ | X | Substitution Position of —CH2—O—Y | Y |
|---|---|---|---|---|---|
| 92 | H2N—C(=NH)— | —H | —CO2Me | meta-position | 3-methylphenyl-CH₂CH₂NH₂ |
| 93 | H2N—C(=NH)— | —H | —CO2Me | meta-position | 3-methylphenyl-(CH₂)₃NH₂ |
| 94 | H2N—C(=NH)— | —H | —CO2Me | meta-position | 3-methylphenyl-NHMe |
| 95 | H2N—C(=NH)— | —H | —CO2Me | meta-position | 3-methylphenyl-NMe₂ |
| 96 | H2N—C(=NH)— | —H | —CO2Me | meta-position | 4-methylphenyl-NHMe |
| 97 | H2N—C(=NH)— | —H | —CO2Me | meta-position | 4-methylphenyl-NMe₂ |
| 98 | H2N—C(=NH)— | —H | —CO2Me | meta-position | 4-methylphenyl-Me |
| 99 | H2N—C(=NH)— | —H | —CO2Me | meta-position | 4-methylphenyl-CH₂Me |
| 100 | H2N—C(=NH)— | —H | —CO2Me | meta-position | 4-methylphenyl-CH(Me)₂ |

TABLE 1-continued

| Compound Number | A | R¹ | X | Substitution Position of —CH2—O—Y | Y |
|---|---|---|---|---|---|
| 101 | H2N—C(=NH)— | —H | —CO2Me | meta-position | 4-(2-methyl-2-propyl)phenyl (cumyl-type, p-C(Me)₃... p-C(CH₃)₂Me) |
| 102 | H2N—C(=NH)— | —H | —CO2Me | meta-position | 2-chlorophenyl |
| 103 | H2N—C(=NH)— | —H | —CO2Me | meta-position | 3-chlorophenyl |
| 104 | H2N—C(=NH)— | —H | —CO2Me | meta-position | 4-chlorophenyl |
| 105 | H2N—C(=NH)— | —H | —CO2Me | meta-position | 2-hydroxyphenyl |
| 106 | H2N—C(=NH)— | —H | —CO2Me | meta-position | 3-hydroxyphenyl |
| 107 | H2N—C(=NH)— | —H | —CO2Me | meta-position | 4-hydroxyphenyl |
| 108 | H2N—C(=NH)— | —H | —CO2Me | meta-position | 3-(hydroxymethyl)phenyl |
| 109 | H2N—C(=NH)— | —H | —CO2Me | meta-position | 3-(2-hydroxyethyl)phenyl |

TABLE 1-continued

| Compound Number | A | R¹ | X | Substitution Position of —CH2—O—Y | Y |
|---|---|---|---|---|---|
| 110 | H2N—C(=NH)— | —H | —CO2Me | meta-position | 2-amino-3-methylpyridine |
| 111 | H2N—C(=NH)— | —H | —CO2Me | meta-position | 2-methyl-5-methylaniline |
| 112 | H2N—C(=NH)— | —H | —CO2Me | meta-position | 2-methyl-4-chloro-5-methylaniline |
| 113 | H2N—C(=NH)— | —H | —CO2Me | meta-position | 5-methyl-2-methylphenol |
| 114 | H2N—C(=NH)— | —H | —CO2Me | meta-position | benzyl |
| 115 | H2N—C(=NH)— | —H | —CO2Me | meta-position | 4-methylbenzyl |
| 116 | H2N—C(=NH)— | —H | —CO2Me | meta-position | 4-ethylbenzyl |
| 117 | H2N—C(=NH)— | —H | —CO2Me | meta-position | 4-isopropylbenzyl |

TABLE 1-continued
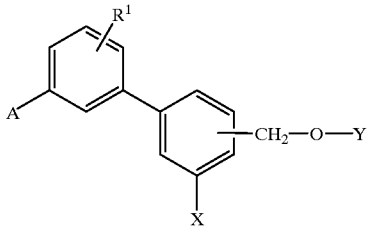
| Compound Number | A | R[1] | X | Substitution Position of —CH2—O—Y | Y |
|---|---|---|---|---|---|
| 118 | H2N—C(=NH)— | —H | —CO2Me | meta-position | 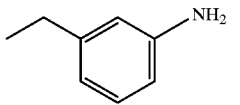 |
| 119 | H2N—C(=NH)— | —H | —CO2Me | meta-position | 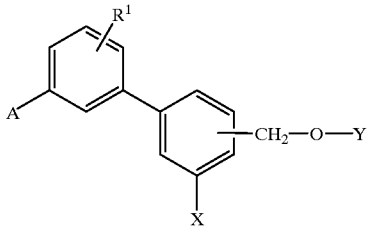 |
| 120 | H2N—C(=NH)— | —H | —CO2Me | meta-position | 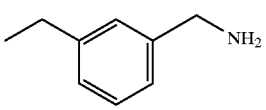 |
| 121 | H2N—C(=NH)— | —H | —CO2Me | meta-position | 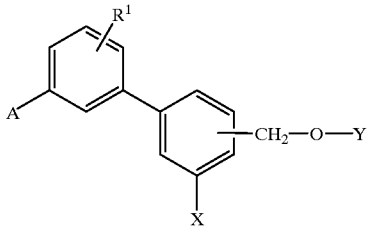 |
| 122 | H2N—C(=NH)— | —H | —CO2Me | meta-position | 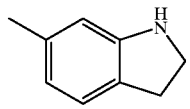 |
| 123 | H2N—C(=NH)— | —H | —CO2Me | meta-position | 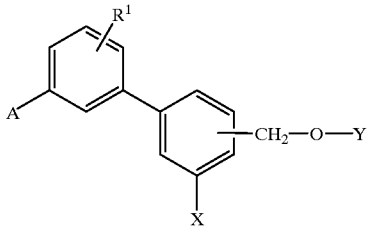 |
| 124 | H2N—C(=NH)— | —H | —CO2Me | meta-position | 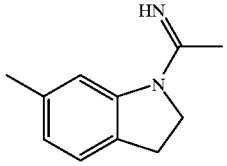 |
| 125 | H2N—C(=NH)— | —H | —CO2Me | meta-position | 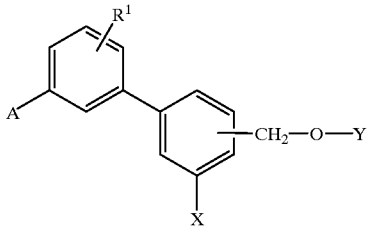 |
| 126 | H2N—C(=NH)— | —H | —CO2Me | meta-position | 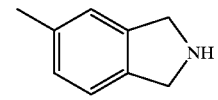 |

TABLE 1-continued
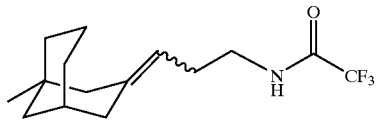
| Compound Number | A | R¹ | X | Substitution Position of —CH2—O—Y | Y |
|---|---|---|---|---|---|
| 127 | H2N—C(=NH)— | —H | —CO2Me | meta-position | 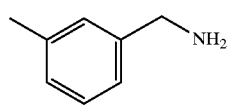 |
| 128 | H2N—C(=NH)— | —H | —CO2Et | meta-position | 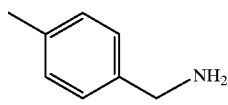 |
| 129 | H2N—C(=NH)— | —H | —CO2Et | meta-position | 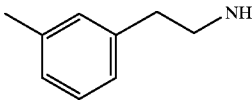 |
| 130 | H2N—C(=NH)— | —H | —CO2Et | meta-position | 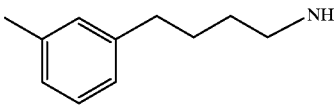 |
| 131 | H2N—C(=NH)— | —H | —CO2Et | meta-position | 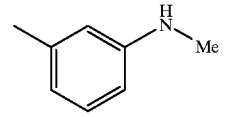 |
| 132 | H2N—C(=NH)— | —H | —CO2Et | meta-position | 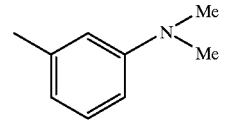 |
| 133 | H2N—C(=NH)— | —H | —CO2Et | meta-position | 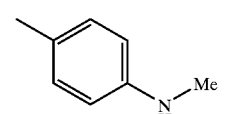 |
| 134 | H2N—C(=NH)— | —H | —CO2Et | meta-position | 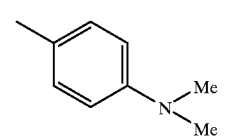 |
| 135 | H2N—C(=NH)— | —H | —CO2Et | meta-position | |

TABLE 1-continued
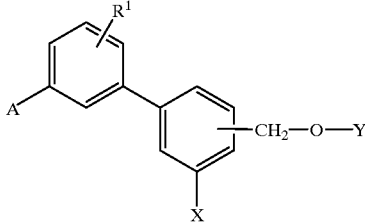
| Compound Number | A | R¹ | X | Substitution Position of —CH2—O—Y | Y |
|---|---|---|---|---|---|
| 136 | H2N—C(=NH)— | —H | —CO2Et | meta-position | 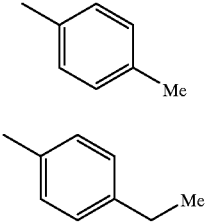 |
| 137 | H2N—C(=NH)— | —H | —CO2Et | meta-position | |
| 138 | H2N—C(=NH)— | —H | —CO2Et | meta-position | |
| 139 | H2N—C(=NH)— | —H | —CO2Et | meta-position | 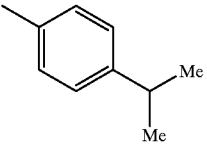 |
| 140 | H2N—C(=NH)— | —H | —CO2Et | meta-position | 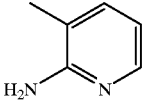 |
| 141 | H2N—C(=NH)— | —H | —CO2Et | meta-position | 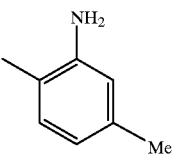 |
| 142 | H2N—C(=NH)— | —H | —CO2Et | meta-position | 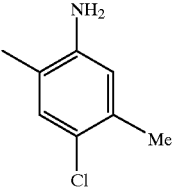 |
| 143 | H2N—C(=NH)— | —H | —CO2Ph | meta-position | 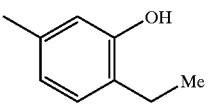 |
| 144 | H2N—C(=NH)— | —H | —CO2Ph | meta-position | 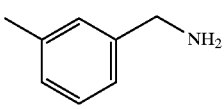 |

TABLE 1-continued
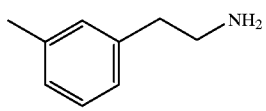
| Compound Number | A | R¹ | X | Substitution Position of —CH2—O—Y | Y |
|---|---|---|---|---|---|
| 145 | H2N—C(=NH)— | —H | —CO2Ph | meta-position | 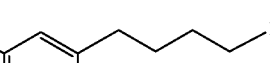 |
| 146 | H2N—C(=NH)— | —H | —CO2Ph | meta-position |  |
| 147 | H2N—C(=NH)— | —H | —CO2Ph | meta-position | 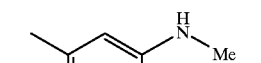 |
| 148 | H2N—C(=NH)— | —H | —CO2Ph | meta-position | 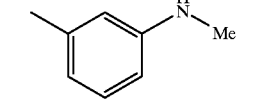 |
| 149 | H2N—C(=NH)— | —H | —CO2Ph | meta-position | 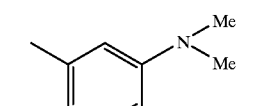 |
| 150 | H2N—C(=NH)— | —H | —CO2Ph | meta-position | 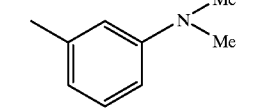 |
| 151 | H2N—C(=NH)— | —H | —CO2Ph | meta-position | 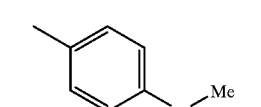 |
| 152 | H2N—C(=NH)— | —H | —CO2Ph | meta-position | 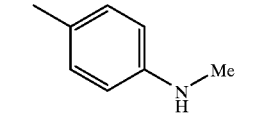 |
| 153 | H2N—C(=NH)— | —H | —CO2Ph | meta-position | 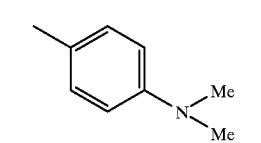 |

TABLE 1-continued
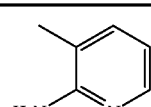
| Compound Number | A | R¹ | X | Substitution Position of —CH2—O—Y | Y |
|---|---|---|---|---|---|
| 154 | H2N—C(=NH)— | —H | —CO2Ph | meta-position | 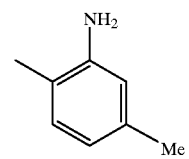 |
| 155 | H2N—C(=NH)— | —H | —CO2Ph | meta-position | 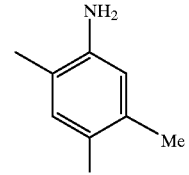 |
| 156 | H2N—C(=NH)— | —H | —CO2Ph | meta-position | 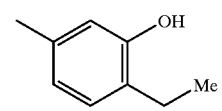 |
| 157 | H2N—C(=NH)— | —H | —CO2Ph | meta-position | 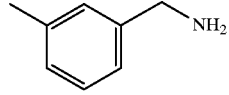 |
| 158 | H2N—C(=NH)— | —H | —CO2CH2Ph | meta-position | 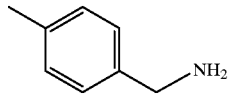 |
| 159 | H2N—C(=NH)— | —H | —CO2CH2Ph | meta-position | 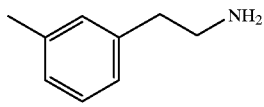 |
| 160 | H2N—C(=NH)— | —H | —CO2CH2Ph | meta-position | 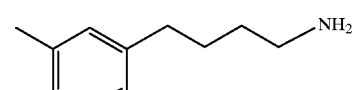 |
| 161 | H2N—C(=NH)— | —H | —CO2CH2Ph | meta-position | 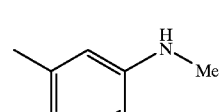 |
| 162 | H2N—C(=NH)— | —H | —CO2CH2Ph | meta-position | |

TABLE 1-continued

| Compound Number | A | R¹ | X | Substitution Position of —CH2—O—Y | Y |
|---|---|---|---|---|---|
| 163 | H2N—C(=NH)— | —H | —CO2CH2Ph | meta-position | 3-(N,N-dimethylamino)-methylphenyl |
| 164 | H2N—C(=NH)— | —H | —CO2CH2Ph | meta-position | 4-(N-methylamino)-methylphenyl |
| 165 | H2N—C(=NH)— | —H | —CO2CH2Ph | meta-position | 4-(N,N-dimethylamino)-methylphenyl |
| 166 | H2N—C(=NH)— | —H | —CO2CH2Ph | meta-position | 4-methylphenyl (with methyl) |
| 167 | H2N—C(=NH)— | —H | —CO2CH2Ph | meta-position | 4-ethylphenyl |
| 168 | H2N—C(=NH)— | —H | —CO2CH2Ph | meta-position | 4-isopropylphenyl |
| 169 | H2N—C(=NH)— | —H | —CO2CH2Ph | meta-position | 2-amino-3-methylpyridyl |
| 170 | H2N—C(=NH)— | —H | —CO2CH2Ph | meta-position | 2-amino-4-methylphenyl (with Me) |

TABLE 1-continued

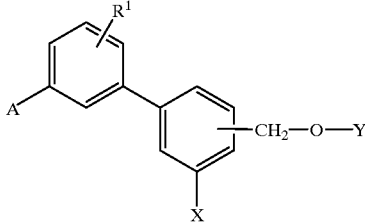

| Compound Number | A | R¹ | X | Substitution Position of —CH2—O—Y | Y |
|---|---|---|---|---|---|
| 171 | H2N—C(=NH)— | —H | —CO2CH2Ph | meta-position | 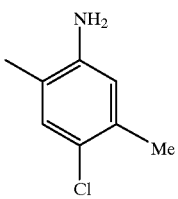 |
| 172 | H2N—C(=NH)— | —H | —CO2CH2Ph | meta-position | 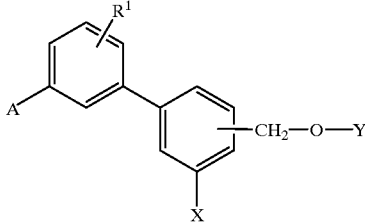 |
| 173 | H2N—C(=NH)— | —H | —H | meta-position | 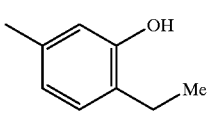 |
| 174 | H2N—C(=NH)— | —H | —H | meta-position | 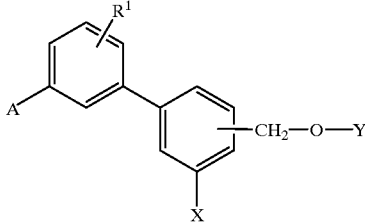 |
| 175 | H2N—C(=NH)— | —OH at meta-position | —CO2H | meta-position |  |
| 176 | H2N—C(=NH)— | —OH at meta-position | —CO2H | meta-position | 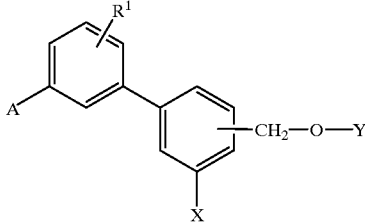 |
| 177 | H2N—C(=NH)— | —OH at meta-position | —CO2H | meta-position |  |
| 178 | H2N—C(=NH)— | —OH at meta-position | —CO2H | meta-position | 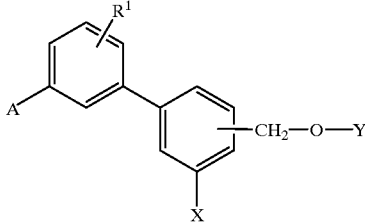 |
| 179 | H2N—C(=NH)— | —OH at meta-position | —CO2H | meta-position | 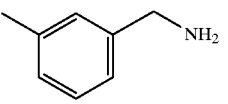 |

TABLE 1-continued

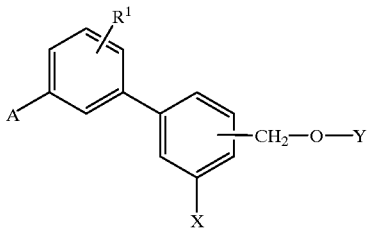

| Compound Number | A | R¹ | X | Substitution Position of —CH2—O—Y | Y |
|---|---|---|---|---|---|
| 180 | H2N—C(=NH)— | —OH at meta-position | —CO2H | meta-position | 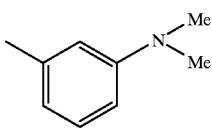 |
| 181 | H2N—C(=NH)— | —OH at meta-position | —CO2H | meta-position | 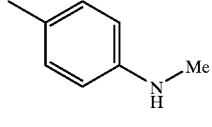 |
| 182 | H2N—C(=NH)— | —OH at meta-position | —CO2H | meta-position | 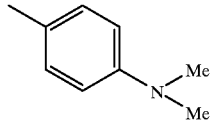 |
| 183 | H2N—C(=NH)— | —Me at meta-position | —CO2H | meta-position | 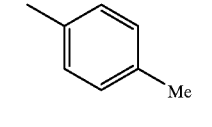 |
| 184 | H2N—C(=NH)— | —Me at meta-position | —CO2H | meta-position | 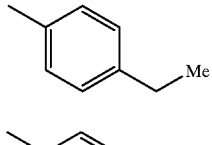 |
| 185 | H2N—C(=NH)— | —Me at meta-position | —CO2H | meta-position | 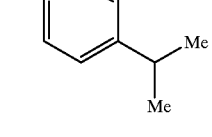 |
| 186 | H2N—C(=NH)— | —Me at meta-position | —CO2H | meta-position | 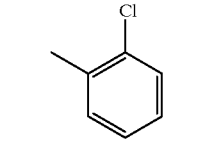 |
| 187 | H2N—C(=NH)— | —Me at meta-position | —CO2H | meta-position | 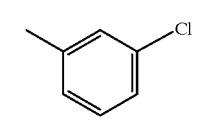 |
| 188 | H2N—C(=NH)— | —OH at meta-position | —CO2H | meta-position | 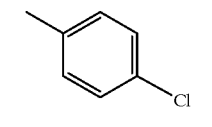 |

TABLE 1-continued

| Compound Number | A | R¹ | X | Substitution Position of —CH2—O—Y | Y |
|---|---|---|---|---|---|
| 189 | H2N—C(=NH)— | —Me at meta-position | —CO2H | meta-position | 2-methylphenol (o-cresol) |
| 190 | H2N—C(=NH)— | —Me at meta-position | —CO2H | meta-position | 3-methylphenol (m-cresol) |
| 191 | H2N—C(=NH)— | —Me at meta-position | —CO2H | meta-position | 4-methylphenol (p-cresol) |
| 192 | H2N—C(=NH)— | —Me at meta-position | —CO2H | meta-position | (3-methylphenyl)methanol |
| 193 | H2N—C(=NH)— | —Me at meta-position | —CO2H | meta-position | 2-(3-methylphenyl)ethanol |
| 194 | H2N—C(=NH)— | —Me at meta-position | —CO2H | meta-position | 2-amino-3-methylpyridine |
| 195 | H2N—C(=NH)— | —Me at meta-position | —CO2H | meta-position | 2,5-dimethylaniline |
| 196 | H2N—C(=NH)— | —Me at meta-position | —CO2H | meta-position | 4-chloro-2,5-dimethylaniline |

TABLE 1-continued

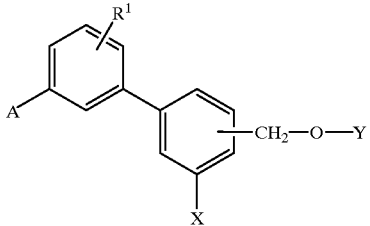

| Compound Number | A | R¹ | X | Substitution Position of —CH2—O—Y | Y |
|---|---|---|---|---|---|
| 197 | H2N—C(=NH)— | —Me at meta-position | —CO2H | meta-position | 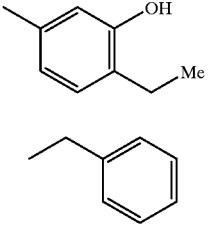 |
| 198 | H2N—C(=NH)— | —OH at meta-position | —CO2H | meta-position | 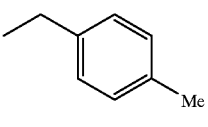 |
| 199 | H2N—C(=NH)— | —Me at meta-position | —CO2H | meta-position | 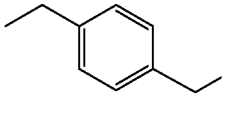 |
| 200 | H2N—C(=NH)— | —Me at meta-position | —CO2H | meta-position | 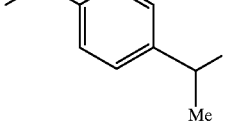 |
| 201 | H2N—C(=NH)— | —Me at meta-position | —CO2H | meta-position | 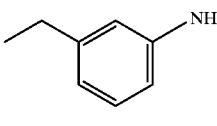 |
| 202 | H2N—C(=NH)— | —OH at meta-position | —CO2H | meta-position | 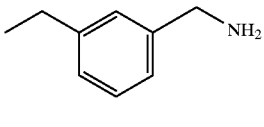 |
| 203 | H2N—C(=NH)— | —OH at meta-position | —CO2H | meta-position | 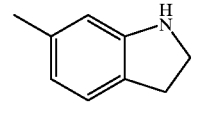 |
| 204 | H2N—C(=NH)— | —OH at meta-position | —CO2H | meta-position | 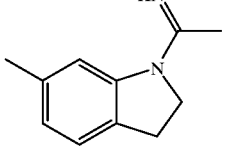 |
| 205 | H2N—C(=NH)— | —OH at meta-position | —CO2H | meta-position |  |

TABLE 1-continued

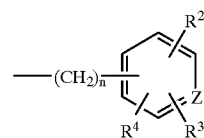

| Compound Number | A | R¹ | X | Substitution Position of —CH2—O—Y | Y |
|---|---|---|---|---|---|
| 206 | H2N—C(=NH)— | —OH at meta-position | —CO2H | meta-position | 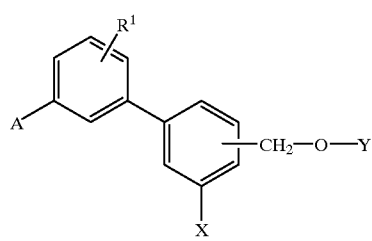 |
| 207 | H2N—C(=NH)— | —OH at meta-position | —CO2H | meta-position | |
| 208 | H2N—C(=NH)— | —OH at meta-position | —CO2H | meta-position | |
| 209 | H2N—C(=NH)— | —OH at meta-position | —CO2H | meta-position | |

What is claimed is:

1. A biphenylamidine compound represented by the formula (1), or a pharmaceutically acceptable salt thereof:

(1)

(wherein, A represents an amidino group; $R^1$ represents a hydrogen atom, a hydroxyl group, an amino group, a nitro group, a $C_1$–$C_8$ alkyl group, or a $C_1$–$C_8$ alkoxy group; X represents a carboxyl group, an aralkoxycarbonyl group, an aryloxycarbonyl group, a $C_1$–$C_8$ alkoxycarbonyl group, or a hydrogen atom (provided that Y was limited to a case represented by the below-mentioned formula (1-4) when X represents the hydrogen atom); Y represents a group of the following formula (1-1):

(1-1)

(wherein, n represents 0 or 1; Z represents C—H or a nitrogen atom; $R^2$ represents a hydrogen atom, an amino group, an amino $C_1$–$C_4$ alkyl group, a $C_1$–$C_4$ alkylamino group or a di-$C_1$–$C_4$ alkylamino group; $R^3$ represents a hydrogen atom, or a $C_1$–$C_4$ alkyl group; $R^4$ represents a hydrogen atom, a fluorine atom, a chlorine atom, a bromine atom, a hydroxide group, or a hydroxy $C_1$–$C_4$ alkyl group), or a group of the following formula (1-2):

(1-2)

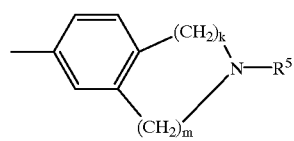

(wherein, k and m each represents an integer of from 0 to 2 (provided that k+m=2); $R^5$ represents a hydrogen atom, an amidino group, or a group of the following formula (1-3):

(1-3)

(wherein, $R^6$ represents a $C_1$–$C_4$ alkyl group, an aralkyl group or a phenyl group), or a group of the following formula (1-4):

(1-4)

(wherein, the wavy line represents an E isomer, a Z isomer or their mixture on the basis of the double bond in an arbitrary ratio; $R^7$ represents a hydrogen atom or a trifluoroacetyl group).

2. A biphenylamidine compound represented by the formula (2) or a pharmaceutically acceptable salt thereof according to claim 1:

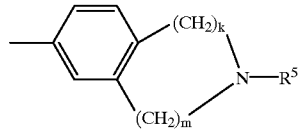
(2)

(wherein, A represents an amidino group; $R^1$ represents a hydrogen atom, a hydroxyl group, or a $C_1$–$C_4$ alkoxy group; X represents a carboxyl group, an aralkoxycarbonyl group, an aryloxycarbonyl group, a $C_1$–$C_8$ alkoxycarbonyl group, or a hydrogen atom (provided that Y is limited to a case represented by the below-mentioned formula (2-4) when X represents the hydrogen atom); Y represents a group of the following formula (2-1):

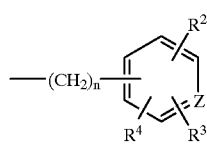
(2-1)

(wherein, n represents 0 or 1; Z represents C—H or a nitrogen atom; $R^2$ represents a hydrogen atom, an amino group, an amino $C_1$–$C_4$ alkyl group, a methylamino group, or a dimethylamino group; $R^3$ represents a hydrogen atom or a $C_1$–$C_4$ alkyl group; $R^4$ represents a hydrogen atom, a chlorine atom, a hydroxyl group, a hydroxymethyl group, or a hydroxyethyl group), or a group of the following formula (2-2):

(2—2)

(wherein, k and m each represents an integer of from 0 to 2, (provided that k+m=2); $R^5$ is a hydrogen atom, or a group of the following formula (2-3):

(2-3)

(wherein, $R^6$ represents a $C_1$–$C_4$ alkyl group), or a group of the following formula (2—4):

(2—4)

(wherein, the wavy line represents an E isomer, a Z isomer, or their mixture on the basis of the double bond in an arbitrary ratio; $R^7$ represents a hydrogen atom or a trifluoroacetyl group).

3. A biphenylamidine compound represented by the formula (3) or a pharmaceutically acceptable salt thereof according to claim 1 or 2:

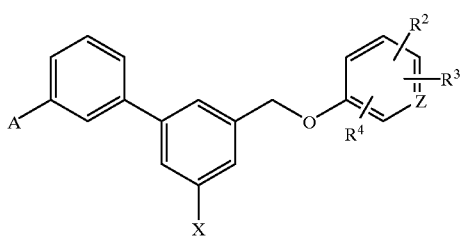
(3)

(wherein, A represents an amidino group; X represents a carboxyl group, an aralkoxycarbonyl group, an aryloxycarbonyl group, or a $C_1$–$C_8$ alkoxycarbonyl group; Z represents CH or a nitrogen atom; $R^2$ represents a hydrogen atom, an amino group, an aminomethyl group, an aminoethyl group, a methylamino group, or a dimethylamino group; $R^3$ represents a hydrogen atom or a $C_1$–$C_4$ alkyl group; $R^4$ represents a hydrogen atom, a chlorine atom, a hydroxyl group, a hydroxymethyl group, or a hydroxyethyl group).

4. A biphenylamidine compound represented by the formula (4) or a pharmaceutically acceptable salt thereof according to claim 1 or 2:

(4)

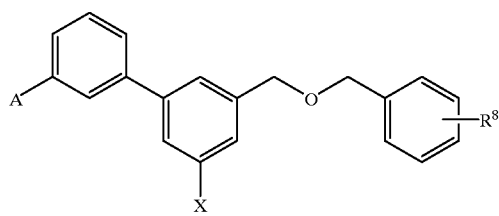

(wherein, A represents an amidino group; X represents a carboxyl group, an aralkoxycarbonyl group, an aryloxycarbonyl group, or a $C_1$–$C_8$ alkoxycarbonyl group; $R^8$ represents a hydrogen atom, an amino group, an aminomethyl group, an aminoethyl group, or a $C_1$–$C_4$ alkyl group).

5. A biphenylamidine compound represented by the formula (5) or a pharmaceutically acceptable salt thereof according to claim 1 or 2:

(5)

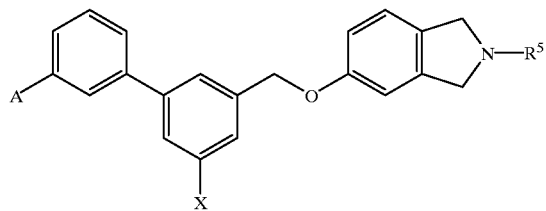

(wherein, A represents an amidino group; X represents a carboxyl group, an aralkoxycarbonyl group, an aryloxycarbonyl group, or a $C_1$–$C_8$ alkoxycarbonyl group; $R^5$ represents a hydrogen atom or an acetimidoyl group).

6. A biphenylamidine compound represented by the formula (6) or a pharmaceutically acceptable salt thereof according to claim 1 or 2:

(6)

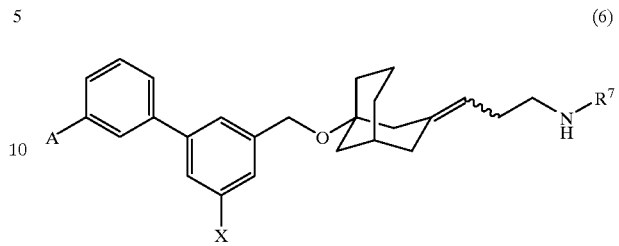

(wherein, the wavy line represents an E isomer, a Z isomer, or their mixture on the basis of the double bond in an arbitrary ratio; A represents an amidino group; X represents a carboxyl group, an aralkoxycarbonyl group, an aryloxycarbonyl group, a $C_1$–$C_8$ alkoxycarbonyl group, or a hydrogen atom; $R^7$ represents a hydrogen atom or a trifluoroacetyl group).

7. A prodrug compound which produces a biphenylamidine compound or a pharmaceutically acceptable salt thereof according to claim 1 or claim 2, in vivo.

8. An anticoagulant inhibitor which comprises a biphenylamidine compound or a pharmaceutically acceptable salt thereof according to claim 1 and a pharmaceutically acceptable carrier.

9. A thrombus or embolus-preventing composition which comprises a biphenylamidine compound or a pharmaceutically acceptable salt thereof according to claim 1 and a pharmaceutically acceptable carrier.

10. A thrombus or embolus-treating composition which comprises a biphenylamidine compound or a pharmaceutically acceptable salt thereof according to claim 1 and a pharmaceutically acceptable carrier.

* * * * *